United States Patent

Müller et al.

[11] Patent Number: 5,935,986
[45] Date of Patent: Aug. 10, 1999

[54] AZOLYL OXYBENZYL ALKOXYACRYLIC ACID ESTERS, PROCESS FOR PRODUCING THEM AND THEIR USE

[75] Inventors: Bernd Müller, Frankenthal; Reinhard Kirstgen, Neustadt; Hartmann König, Heidelberg; Michael Rack, Heidelberg; Klaus Oberdorf, Heidelberg; Franz Röhl, Schifferstadt; Hubert Sauter, Mannheim; Gisela Lorenz, Hambach; Eberhard Ammermann, Heppenheim; Siegfried Strathmann, Limburgerhof; Volker Harries, Frankenthal, all of Germany

[73] Assignee: BASF Aktiengesellschaft, Ludwigshafen, Germany

[21] Appl. No.: 08/952,755

[22] PCT Filed: May 13, 1996

[86] PCT No.: PCT/EP96/02042

§ 371 Date: Nov. 20, 1997

§ 102(e) Date: Nov. 20, 1997

[87] PCT Pub. No.: WO96/37477

PCT Pub. Date: Nov. 28, 1996

[30] Foreign Application Priority Data

May 24, 1995 [DE] Germany .............. 195 19 041

[51] Int. Cl.$^6$ ................ A01N 43/56; C07D 231/20; C07D 231/22
[52] U.S. Cl. .................. 514/407; 514/340; 514/384; 514/538; 514/727; 514/730; 548/366.1; 548/368.1; 548/370.4; 548/370.7; 548/371.1; 560/39; 560/61; 564/253; 568/715; 568/807; 546/276.1
[58] Field of Search ............ 514/407; 548/366.1, 548/368.1, 370.4

[56] References Cited

FOREIGN PATENT DOCUMENTS

| 254 426 | 1/1988 | European Pat. Off. . |
|---|---|---|
| 278 595 | 8/1988 | European Pat. Off. . |
| 299 694 | 1/1989 | European Pat. Off. . |
| 581 095 | 2/1994 | European Pat. Off. . |
| 94/00436 | 1/1994 | WIPO . |
| 94/19331 | 9/1994 | WIPO . |
| 95/25095 | 9/1995 | WIPO . |

*Primary Examiner*—Robert W. Ramsuer
*Assistant Examiner*—Jane C. Osowecki
*Attorney, Agent, or Firm*—Keil & Weinkauf

[57] ABSTRACT

There are described compounds of the general formula I

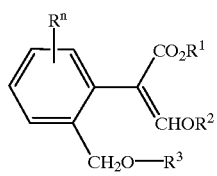

in which the index and the substituents have the following meanings:

n is 0, 1, 2, 3 or 4;

R is nitro, cyano, halogen,
unsubstituted or substituted alkyl, alkenyl, alkynyl, alkoxy, alkenyloxy, alkynyloxy or
in the event that n is greater than 1 additionally an unsubstituted or substituted bridge which is bonded to two adjacent ring atoms;

$R^1$, $R^2$ are alkyl;

$R^3$ is a substituted pyrazole [sic] or triazole [sic] radical of the formulae A.1 to A.3

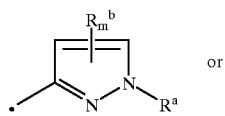

A.1

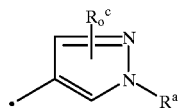

A.2 where the bond marked ● is the bond to the oxygen, processes for their preparation, and their use.

9 Claims, No Drawings

AZOLYL OXYBENZYL ALKOXYACRYLIC ACID ESTERS, PROCESS FOR PRODUCING THEM AND THEIR USE

This application is a 371 of PCT/EP96/02042 filed May 13, 1996.

The present invention relates to compounds of the general formula I

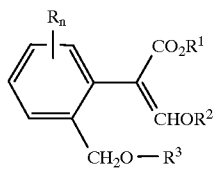

in which the index and the substituents have the following meanings:

n is 0, 1, 2, 3 or 4, it being possible for the substituents R to differ if n is greater than 1;

R is nitro, cyano, halogen,
unsubstituted or substituted alkyl, alkenyl, alkynyl, alkoxy, alkenyloxy, alkynyloxy or
in the event that n is greater than 1 additionally an unsubstituted or substituted bridge which is bonded to two adjacent ring atoms and which three to four members selected from the group consisting of 3 or 4 carbon atoms, 1, 2 or 3 carbon atoms and 1 or 2 nitrogen, oxygen and/or sulfur atoms, it being possible for this bridge, together with the ring to which it is bonded, to form a partially unsaturated or aromatic radical;

$R^1$, $R^2$ are $C_1$–$C_4$-alkyl;

$R^3$ is a pyrazole or triazole radical of the formulae A.1 to A.3

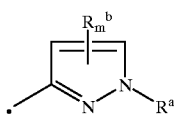

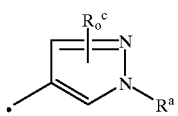

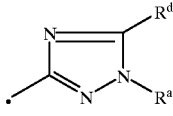

the bond marked with ● being the bond to the oxygen and the indices and the substituents having the following meanings:

$R^a$ is unsubstituted or substituted alkyl, alkenyl or alkynyl;
an unsubstituted or substituted saturated or mono- or diunsaturated ring which, besides carbon atoms, can contain one to three of the following hetero atoms as ring members: oxygen, sulfur and nitrogen; or
a substituted mono- or binuclear aromatic radical which, besides carbon atoms, can contain one to four nitrogen atoms or one or two nitrogen atoms and one or two oxygen or sulfur atoms or one oxygen or one sulfur atom as ring members;

m is 0, 1 or 2, it being possible for the substituents $R^b$ to differ if m is greater than 1;

$R^b$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl;

o is 0, 1 or 2, it being possible for the substituents $R^c$ to differ if o is greater than 1;

$R^c$ is halogen,
unsubstituted or substituted alkyl, alkenyl or alkynyl;
an unsubstituted or substituted saturated or mono- or diunsaturated ring which, besides carbon atoms, can contain one to three of the following hetero atoms as ring members: oxygen, sulfur and nitrogen; or
an unsubstituted or substituted mono- or binuclear aromatic radical which, besides carbon atoms, can contain one to four nitrogen atoms or one or two nitrogen atoms and one or two oxygen or sulfur atoms or one oxygen or one sulfur atom as ring members;

$R^d$ is hydrogen, cyano, halogen,
unsubstituted or substituted alkyl, alkoxy, alkenyl, alkenyloxy, alkynyl, alkynyloxy;
an unsubstituted or substituted saturated or mono- or diunsaturated ring which, besides carbon atoms, can contain one to three of the following hetero atoms as ring members: oxygen, sulfur and nitrogen; and which can be bonded to the skeleton either directly or via an oxygen or sulfur atom; or
a substituted mono- or binuclear aromatic radical which, besides carbon atoms, can contain one to four nitrogen atoms or one or two nitrogen atoms and one or two oxygen or sulfur atoms or one oxygen or one sulfur atom as ring members.

The invention furthermore relates to processes for the preparation of these compounds, to compositions comprising them, and to their use for controlling animal and fungal pests.

The literature describes hetaryloxybenzylalkoxyacrylic esters having a fungicidal and, in some cases, also insecticidal, acaricidal and nematicidal action in general form (EP-A 278 595; EP-A 254 426; EP-A 358 692; WO-A 94/19,331, WO-A 94/00,436).

It was an object of the present invention to provide compounds with an improved activity.

Accordingly, we have found that this object is achieved by the compounds I defined at the outset. Furthermore, processes for the preparation of these compounds, compositions comprising them, and their use for controlling animal and fungal pests have been found.

The compounds I are accessible via a variety of methods which are known per se from the literature cited.

For example, the compounds I are obtained by reacting the benzyl derivative II with a hydroxyazole of the formula III in the presence of a base.

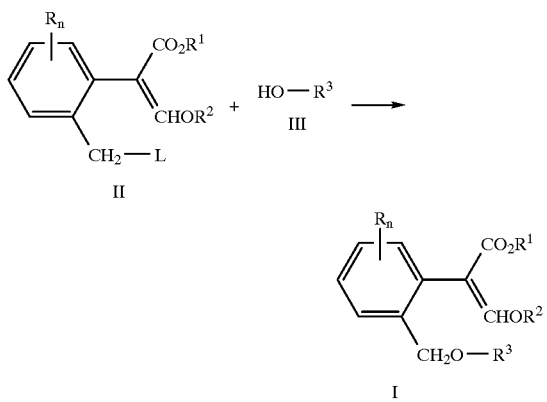

L in formula II is a nucleophilically exchangeable group, for example halogen, eg. chlorine, bromine and iodine, or an alkyl- or arylsulfonate, eg. methylsulfonate, trifluoromethylsulfonate, phenylsulfonate and 4-methylphenylsulfonate.

The reaction is conventionally carried out at from 0° C. to 100° C., preferably 20° C. to 60° C.

Suitable solvents are aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, alcohols, such as methanol, ethanol, n-propanol, i-propanol, n-butanol and tert-butanol, ketones, such as acetone and methyl ethyl ketone, and also ethyl acetate, dimethyl sulfoxide, dimethylformamide, N-methylpyrrolidone, dimethylacetamide, 1,3-dimethylimidazolidin-2-one and 1,2-dimethyltetrahydro-2(1H)-pyrimidine, preferably methylene chloride, acetone, N-methylpyrrolidone and dimethylformamide. Mixtures of these can also be used.

Bases which are generally suitable are inorganic compounds, such as alkali metal hydroxides and alkaline earth metal hydroxides (eg. lithium hydroxide, sodium hydroxide, potassium hydroxide and calcium hydroxide), alkali metal oxides and alkaline earth metal oxides (eg. lithium oxide, sodium oxide, calcium oxide and magnesium oxide), alkali metal hydrides and alkaline earth metal hydrides (eg. lithium hydride, sodium hydride, potassium hydride and calcium hydride), alkali metal amides (eg. lithium amide, sodium amide and potassium amide), alkali metal carbonates and alkaline earth metal carbonates (eg. lithium carbonate, potassium carbonate and calcium carbonate), and also alkali metal hydrogen carbonates (eg. sodium hydrogen carbonate), organometal compounds, in particular alkali metal alkyls (eg. methyllithium, butyllithium and phenyllithium), alkylmagnesium halides (eg. methylmagnesium chloride) and alkali metal alcoholates and alkaline earth metal alcoholates (eg. sodium methanolate, sodium ethanolate, potassium ethanolate, potassium tert-butanolate and dimethoxymagnesium), furthermore organic bases, eg. tertiary amines, such as trimethylamine, triethylamine, triisopropylethylamine and n-methylpiperidine, pyridine, substituted pyridines, such as collidine, lutidine and 4-dimethylaminopyridine, and also bicyclic amines. Substances which are particularly preferred are sodium hydroxide, sodium methanolate, potassium carbonate, potassium methanolate and potassium tert-butanolate.

The bases are generally used in equimolar amounts, in an excess or, if desired, as the solvent.

It may be advantageous for the reaction to add a catalytic amount of a crown ether (eg. 18-crown-6 or 15-crown-5).

The reaction can also be carried out in two-phase systems composed of a solution of alkali metal hydroxides, alkali metal carbonates, alkaline earth metal hydroxides or alkaline earth metal carbonates in water and an organic phase (eg. aromatic and/or halogenated hydrocarbons). Suitable phase transfer catalysts are, for example, ammonium halides and ammonium tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and phosphonium halides (eg. tetrabutylphosphonium chloride and tetraphenylphosphonium bromide).

It may be advantageous for the reaction first to react the hydroxyazole III with the base to give the corresponding hydroxylate, which is then reacted with the benzyl derivative.

Those starting materials II which are required for the preparation of the compounds I which have not already been disclosed in the literature cited at the outset can be prepared by the methods described therein. Those starting materials III which have not already been disclosed in the literature can be prepared by the methods described therein [3-hydroxypyrazoles: J. Heterocycl. Chem. 30, 49 (1993); Chem. Ber. 107, 1318 (1974); Chem. Pharm. Bull. 19, 1389 (1971); Tetrahedron Lett. 11, 875 (1970); Chem. Heterocycl. Comp. 5, 527 (1969); Chem. Ber. 102, 3260 (1969); Chem. Ber. 109, 261 (1976); J. Org. Chem. 31, 1538 (1966); Tetrahedron 43, 607 (1987); 4-hydroxyryrazoles: CA-A 1 177 081; U.S. Pat. No. 4,621,144; JP-A 60/155,160; 3-hydroxytriazoles: Chem. Ber. 56, 1794 (1923); DE-A 21 50 169; DE-A 22 00 436; U.S. Pat. No. 4,433,148; J. Med. Chem. 33, 2772 (1990); Synthesis 1987, 986; DE-A 22 60 015; DE-A 24 17 970].

Moreover, the compounds I are obtained by reacting α-ketoesters of the formula IVc in a Wittig or Wittig-Horner reaction {for example with $(C_6H_5)_3P^+\text{-}CH_2OR^2\ Cl^-$}, as shown by the equation below (cf. EP-A 534 216).

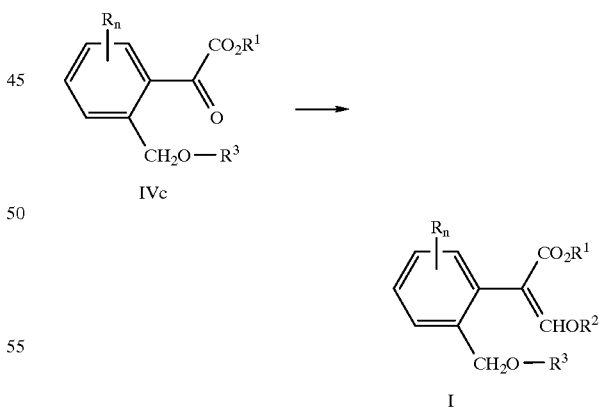

The keto esters can be obtained by a method similar to known processes [cf. EP-A 493 711; Synth. Commun. 21, 2045 (1991); Synth. Commun. 11, 943 (1981)].

The compounds I can furthermore be obtained by first converting a nitrile of the formula Iva with an alcohol ($R^1OH$) to the corresponding benzyl ester IVb, as described in EP-A 493 711, and subsequently converting IVb to I, as described in EP-A 203 608.

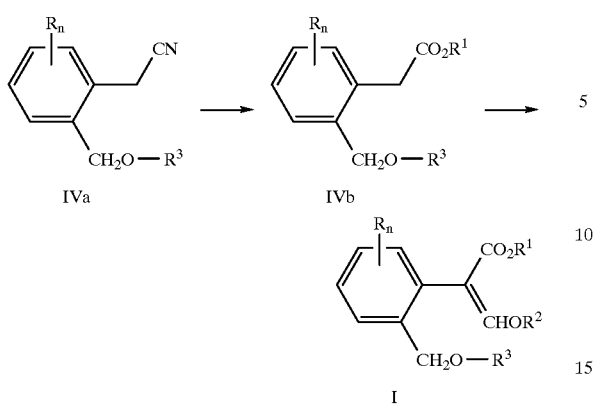

EP-A 596 692 describes the preparation of the nitriles IVa.

With regard to the double bond, the compounds I can be present in the E and the Z configuration. Both isomers can be used according to the invention, either jointly or separately. Particularly preferred is the E isomer (configuration relative to the carboxylate alkoxy group).

In the definitions of the symbols given in the above formulae, collective terms were used which generally represent the following substituents:

halogen: fluorine, chlorine, bromine and iodine;

alkyl: saturated, straight-chain or branched hydrocarbon radicals having 1 to 4 carbon atoms, eg. methyl, ethyl, propyl, 1-methylethyl, butyl, 1-methyl-propyl, 2-methylpropyl and 1,1-dimethylethyl;

haloalkyl: straight-chain or branched alkyl groups having 1 to 4 carbon atoms (as mentioned above), it being possible for some or all of the hydrogen atoms these in groups to be replaced by halogen atoms as mentioned above, eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 carbon atoms (as mentioned above), which are bonded to the skeleton via an oxygen atom (—O—);

alkoxycarbonyl: straight-chain or branched alkoxy groups having 1 to 4 carbon atoms (as mentioned above), which are bonded to the skeleton via a carbonyl group (—CO—);

alkylthio: straight-chain or branched alkyl groups having 1 to 4 carbon atoms (as mentioned above), which are bonded to the skeleton via a sulfur atom (—S—);

unsubstituted or substituted alkyl: saturated, straight-chain or branched hydrocarbon radicals, in particular having 1 to 10 carbon atoms, eg. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

unsubstituted or substituted alkenyl: unsaturated, straight-chain or branched hydrocarbon radicals, in particular having 2 to 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl- 3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

unsubstituted or substituted alkynyl: straight-chain or branched hydrocarbon groups, in particular having 2 to 20 carbon atoms and a triple bond in any position, eg. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

an unsubstituted or substituted saturated or mono- or diunsaturated ring which, besides carbon atoms, can contain one to three of the following hetero atoms as ring members: oxygen, sulfur and nitrogen, for example carbocycles, such as cyclopropyl, cyclopentyl, cyclohexyl, cyclopent-2-enyl, cyclohex-2-enyl, 5- to 6-membered, saturated or unsaturated heterocycles containing one to three nitrogen atoms and/or one oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl;

or an unsubstituted or substituted mono- or dinuclear aromatic ring system which, besides carbon atoms, can contain one to four nitrogen atoms or one or two nitrogen atoms and one oxygen or sulfur atom or one oxygen or sulfur atom as ring members, ie. aryl radicals, such as phenyl and naphthyl, preferably phenyl or 1- or 2-naphthyl, and hetaryl radicals, for example 5-membered heteroaromatic rings containing one to three nitrogen atoms and/or one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered heteroaromatic rings containing one to four nitrogen atoms as hetero atoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The addition "unsubstituted or substituted" in connection with alkyl, alkenyl and alkynyl groups is intended to express that these groups can be partially or fully halogenated (ie. some or all of the hydrogen atoms in these groups can be replaced by identical or different halogen atoms as mentioned above (preferably fluorine, chlorine and bromine, in particular fluorine and chlorine), and/or can have attached to them one to three, in particular one, of the following radicals:

nitro, cyano, $C_1$–$C_4$-alkoxy, $C_1$–$C_4$-alkoxycarbonyl or a group =N—OR$^x$ where R$^x$ is $C_1$–$C_6$-alkyl, $C_3$–$C_6$-alkenyl and $C_3$–$C_6$-alkynyl (R$^x$ is preferably $C_1$–$C_4$-alkyl), or an unsubstituted or substituted mono- or binuclear aromatic ring system which, besides carbon atoms, can contain one to four nitrogen atoms or one or two nitrogen atoms and one oxygen or sulfur atom or one oxygen or sulfur atom as ring members, ie. aryl radicals, such as phenyl and naphthyl, preferably phenyl or 1- or 2-naphthyl, and hetaryl radicals, for example 5-membered heteroaromatic rings containing one to three nitrogen atoms and/or one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered heteroaromatic rings containing one to four nitrogen atoms as hetero atoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The addition "unsubstituted or substituted" in connection with the cyclic (saturated, unsaturated or aromatic) groups is intended to express that these groups can be partially or fully halogenated (ie. some or all of the hydrogen atoms in these groups can be replaced by identical or different halogen atoms as mentioned above (preferably fluorine, chlorine and bromine, in particular fluorine and chlorine), and/or can have attached to them one to three of the following radicals: nitro, cyano, $C_1$–$C_4$-alkyl, $C_1$–$C_4$-alkoxy and $C_1$–$C_4$-alkoxycarbonyl.

The mono- or binuclear aromatic or heteroaromatic systems mentioned in the radicals can, in turn, be partially or fully halogenated, ie. some or all of the hydrogen atoms in these groups can be replaced by halogen atoms, such as fluorine, chlorine, bromine and iodine, preferably fluorine and chlorine.

These mono- or binuclear aromatic or heteroaromatic systems can additionally have attached to them one to three of the following substituents, besides the halogen atoms indicated:

nitro, cyano, thiocyanato;

alkyl, in particular $C_1$–$C_6$-alkyl, as mentioned above, preferably methyl, ethyl, 1-methylethyl, 1,1-dimethylethyl, butyl, hexyl, in particular methyl and 1-methylethyl;

$C_1$–$C_4$-haloalkyl, as mentioned above, preferably trichloromethyl, difluoromethyl, trifluoromethyl, 2,2-difluoroethyl, 2,2,2-trifluoroethyl and pentafluoroethyl;

$C_1$–$C_4$-alkoxy, preferably methoxy, ethoxy, 1-methylethoxy and 1,1-dimethylethoxy, in particular methoxy;

$C_1$–$C_4$-haloalkoxy, in particular $C_1$–$C_2$-haloalkoxy, preferably difluoromethyloxy, trifluoromethyloxy and 2,2,2-trifluoroethyloxy, in particular difluoromethyloxy;

$C_1$–$C_4$-alkylthio, preferably methylthio and 1-methylethylthio, in particular methylthio;

$C_1$–$C_4$-alkylamino, such as methylamino, ethylamino, propylamino, 1-methylethylamino, butylamino, 1-methylpropylamino, 2-methylpropylamino and 1,1-dimethylethylamino, preferably methylamino and 1,1-dimethylethylamino, in particular methylamino, di-$C_1$–$C_4$-alkylamino, such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)-amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably N,N-dimethylamino and N,N-diethylamino, in particular N,N-dimethylamino;

$C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxycarbonyl, such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, pentyloxycarbonyl, 1-methylbutyloxycarbonyl, 2-methylbutyloxycarbonyl, 3-methylbutyloxycarbonyl, 2,2-dimethylpropyloxycarbonyl, 1-ethylpropyloxycarbonyl, hexyloxycarbonyl, 1,1-dimethylpropoxycarbonyl, 1,2-dimethylpropyloxycarbonyl, 1-methylpentyloxycarbonyl, 2-methylpentyloxycarbonyl, 3-methylpentyloxycarbonyl, 4-methylpentyloxycarbonyl, 1,1-dimethylbutyloxycarbonyl, 1,2-dimethylbutyloxycarbonyl, 1,3-dimethylbutyloxycarbonyl, 2,2-dimethylbutyloxycarbonyl, 2,3-dimethylbutyloxycarbonyl, 3,3-dimethylbutyloxycarbonyl, 1-ethylbutyloxycarbonyl, 2-ethylbutyloxycarbonyl, 1,1,2-trimethylpropyloxycarbonyl, 1,2,2-trimethylpropyloxycarbonyl, 1-ethyl-1-methylpropyloxycarbonyl and 1-ethyl-2-methylpropyloxycarbonyl, preferably methoxycarbonyl, ethoxycarbonyl and 1,1-dimethylethoxycarbonyl, in particular ethoxycarbonyl;

$C_1$–$C_6$-alkylaminocarbonyl, such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylaminecarbonyl and ethylaminecarbonyl, in particular methylaminocarbonyl;

di-$C_1$–$C_6$-alkylaminocarbonyl, in particular di-$C_1$–$C_4$-alkylaminocarbonyl, such as N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)-aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-1,1- dimethylethyl)-N-methylaminocarbonyl, N-ethyl-N-propylaminocarbonyl, N-ethyl-N-(1-methylethyl) aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-di-methylethyl)-N-(1-methylethyl) aminocarbonyl, N-butyl-N-(1-methylpropyl) aminocarbonyl, N-butyl-N-(2-methylpropyl) aminocarbonyl, N-butyl-N-(1,1-dimethylethyl) aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl)aminocarbonyl, preferably N,N-dimethylaminocarbonyl and N,N-diethylaminecarbonyl, in particular N,N-dimethylaminocarbonyl;

$C_1$–$C_6$-alkylcarboxyl, such as methylcarboxyl, ethylcarboxyl, propylcarboxyl, 1-methylethyl-carboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl and 1-ethyl-2-methylpropylcarboxyl, preferably methylcarboxyl, ethylcarboxyl and 1,1-dimethylethylcarbonyl, in particular methylcarboxyl and 1,1-dimethylethylcarboxyl;

$C_1$–$C_6$-alkylcarbonylamino, such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino and 1-ethyl-2-methylpropylcarbonylamino, preferably methylcarbonylamino and ethylcarbonylamino, in particular ethylcarbonylamino;

$C_1$–$C_6$-alkylcarbonyl-$C_1$–$C_6$-alkylamino, such as methylcarbonylmethylamino, ethylcarbonylethylamino, n-propylcarbonyl-n-propylamino, i-propylcarbonyl-i-propylamino, methylcarbonylethylamino, methylcarbonyl-n-propylamino, methylcarbonyl-i-propylamino, ethylcarbonylmethylamino, ethylcarbonyl-n-propylamino, ethylcarbonyl-i-propylamino, n-propylcarbonylmethylamino, n-propylcarbonylethylamino, n-propylcarbonyl-i-propylamino, i-propylcarbonylmethylamino, i-propylcarbonylethylamino, i-propylcarbonyl-n-propylamino, preferably methylcarbonylmethylamino, methylcarbonylethylamino, ethylcarbonylmethylamino, in particular methylcarbonylmethylamino;

$C_3$–$C_7$-cycloalkyl, such as cyclopropyl, cyclobutyl, cyclopentyl, cyclohexyl and cycloheptyl, preferably cyclopropyl, cyclopentyl and cyclohexyl, in particular cyclopropyl;

$C_3$–$C_7$-cycloalkoxy, such as cyclopropyloxy, cyclobutyloxy, cyclopentyloxy, cyclohexyloxy and cycloheptyloxy, preferably cyclopentyloxy and cyclohexyloxy, in particular cyclohexyloxy;

$C_3$–$C_7$-cycloalkylthio, such as cyclopropylthio, cyclobutylthio, cyclopentylthio, cyclohexylthio and cycloheptylthio, preferably cyclohexylthio;

$C_3$–$C_7$-cycloalkylamino, such as cyclopropylamino, cyclobutylamino, cyclopentylamino, cyclohexylamino and cycloheptylamino, preferably cyclopropylamino and cyclohexylamino, in particular cyclopropylamino;

further radicals for unsubstituted or substituted mono- or binuclear aromatic or heteroaromatic radicals:
alkenyl, alkynyl, haloalkenyl, haloalkynyl, alkenyloxy, alkynyloxy, haloalkenyloxy, haloalkynyloxy, alkenylthio, alkynylthio, alkylsulfoxy, alkylsulfonyl, alkenylsulfoxy, alkynylsulfoxy, alkynylsulfonyl,
a group $C(R^y)=N—OR^x$, where $R^x$ and $R^y$ are $C_1$–$C_6$-alkyl, $C_3$–$C_6$-alkenyl and $C_3$–$C_6$-alkynyl, $R^x$ and $R^y$ preferably being $C_1$–$C_4$-alkyl, cycloalkenyl, cycloalkenyloxy, cycloalkenylthio, cycloalkenylamino.

With a view to their biological activity, preferred compounds I are those where $R^1$ and $R^2$ are $C_1$–$C_2$-alkyl, in particular methyl.

Furthermore, preferred compounds I are those where n is 0 or 1, in particular 0.

In the event that n is 1, preferred compounds I are those where R is one of the following groups: fluorine, chlorine, cyano, methyl, trifluoromethyl or methoxy.

Also preferred are compounds I where n is 1 and where R is in the 3- or 6-position relative to the acrylate radical.

Besides, preferred compounds I are those where $R^a$ is unsubstituted or substituted $C_1$–$C_4$-alkyl or $C_3$–$C_6$-cycloalkyl.

Likewise preferred compounds I are those where $R^a$ is an unsubstituted or substituted mono- or binuclear aromatic or heteroaromatic radical.

Furthermore, preferred compounds I are those where $R^a$ is an unsubstituted or substituted 6-membered heteroaromatic ring, in particular pyridine and pyrimidine.

Equally preferred compounds I are those where $R^a$ is an unsubstituted or substituted aromatic radical, in particular phenyl.

Particularly preferred compounds I are those where $R^a$ is unsubstituted or substituted phenyl or benzyl. In these cases, suitable substituents in the phenyl radical are preferably halogen, cyano, $C_1$–$C_4$-alkyl, $C_1$–$C_4$-alkoxy, $C_1$–$C_2$-haloalkyl, $C_1$–$C_2$-haloalkoxy, $C_1$–$C_4$-alkoxycarbonyl, phenyl and oxy-$C_1$–$C_2$-alkylidenoxy.

Equally preferred compounds I are those where $R^a$ is an unsubstituted or substituted six-membered heteroaromatic ring, such as pyridyl and pyrimidyl. Suitable substituents of the six-membered heteroaromatic ring are preferably cyano, halogen, $C_1$–$C_4$-alkyl, $C_1$–$C_2$-haloalkyl, $C_1$–$C_4$-alkoxy, $C_1$–$C_2$-haloalkoxy and phenyl.

Besides, preferred compounds I are those where m or o are 0 or 1, in particular 0.

Likewise preferred compounds I are those where $R^b$ is cyano, halogen, $C_1$–$C_4$-alkyl, $C_1$–$C_2$-haloalkyl, $C_1$–$C_4$-alkoxy, $C_1$–$C_2$-haloalkoxy and $C_1$–$C_4$-alkoxycarbonyl, in particular fluorine, chlorine, methyl, trifluoromethyl and methoxycarbonyl.

Also preferred compounds I are those where $R^c$ is $C_1$–$C_4$-alkyl and $C_1$–$C_2$-haloalkyl, in particular methyl and trifluoromethyl.

Equally preferred compounds I are those where $R^c$ is methyl.

Also preferred compounds I are those where $R^d$ is hydrogen.

Likewise preferred compounds I are those where $R^d$ is halogen, $C_1$–$C_4$-alkyl, $C_1$–$C_4$-haloalkyl, $C_1$–$C_4$-alkoxy and $C_1$–$C_4$-haloalkoxy, in particular chlorine, methyl, trifluoromethyl and methoxy.

Particularly preferred compounds I with regard to their use are those compiled in the tables below. On their own (independently of the combination in which they are mentioned) the groups mentioned in the tables for a substituent furthermore represent a particularly preferred embodiment of the substituent in question.

Table 1

Compounds of the general formula I.1 where $R_n$ is hydrogen, $R^b_m$ is hydrogen, and the combination of the index x and the group $R^x$ for any one compound corresponds to one line of Table A

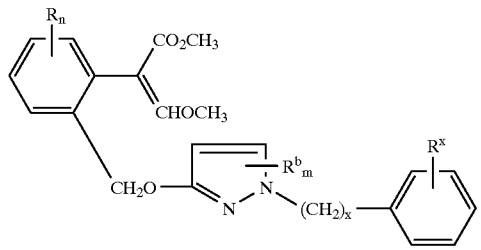

I.1

Table 2

Compounds of the general formula I.1 where $R_n$ is hydrogen, $R^b_m$ is 5-methyl, and the combination of the index x and the group $R^x$ for any one compound corresponds to one line of Table A Table 3

Compounds of the general formula I.1 where $R_n$ is hydrogen, $R^b_m$ is 4-chloro, and the combination of the index x and the group $R^x$ for any one compound corresponds to one line of Table A Table 4

Compounds of the general formula I.1 where $R_n$ is hydrogen, $R^b_m$ is 5-$CF_3$, and the combination of the index x and the group $R^x$ for any one compound corresponds to one line of Table A Table 5

Compounds of the general formula I.1 where $R_n$ is 3-chloro, $R^b_m$ is hydrogen, and the combination of the index x and the group $R^x$ for any one compound corresponds to one line of Table A Table 6

Compounds of the general formula I.1 where $R_n$ is 3-chloro, $R^b_m$ is 5-methyl, and the combination of the index x and the group $R^x$ for any one compound corresponds to one line of Table A Table 7

Compounds of the general formula I.1 where $R_n$ is 3-chloro, $R^b_m$ is 4-chloro, and the combination of the index x and the group $R^x$ for any one compound corresponds to one line of Table A Table 8

Compounds of the general formula I.1 where $R_n$ is 3-chloro, $R^b_m$ is 5-$CF_3$, and the combination of the index x and the group $R^x$ for any one compound corresponds to one line of Table A Table 9

Compounds of the general formula I.2 where $R_n$ is hydrogen, $R^c_o$ is hydrogen, and the combination of the index x and the group $R^x$ for any one compound corresponds to one line of Table A

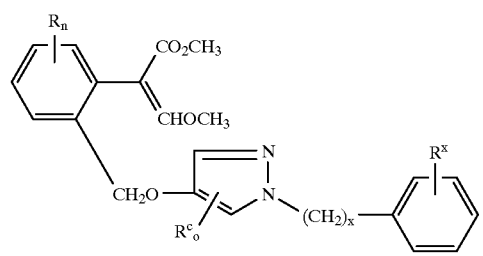

I.2

Table 10

Compounds of the general formula I.2 where $R_n$ is hydrogen, $R^c_o$ is 3-methyl, and the combination of the index x and the group $R^x$ for any one compound corresponds to one line of Table A Table 11

Compounds of the general formula I.2 where $R_n$ is 3-chloro, $R^c_o$ is hydrogen, and the combination of the index x and the group $R^x$ for any one compound corresponds to one line of Table A Table 12

Compounds of the general formula I.2 where $R_n$ is 3-chloro, $R^c_o$ is 3-methyl, and the combination of the index x and the group $R^x$ for any one compound corresponds to one line of Table A Table 13

Compounds of the general formula I.3 where $R_n$ is hydrogen, $R^d$ is hydrogen, and the combination of the index x and the group $R^x$ for any one compound corresponds to one line of Table A

I.3

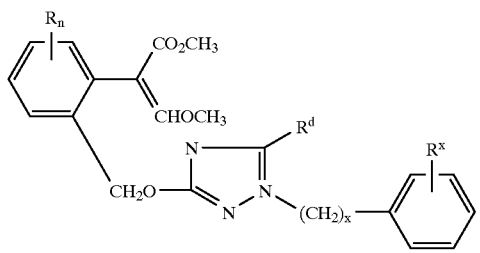

Table 14
Compounds of the general formula I.3 where $R_n$ is hydrogen, $R^d$ is methyl, and the combination of the index x and the group $R^x$ for any one compound corresponds to one line of Table A Table 15
Compounds of the general formula I.3 where $R_n$ is hydrogen, $R^d$ is chlorine, and the combination of the index x and the group $R^x$ for any one compound corresponds to one line of Table A Table 16
Compounds of the general formula 1.3 where $R_n$ is hydrogen, $R^d$ is methoxy, and the combination of the index x and the group $R^x$ for any one compound corresponds to one line of Table A Table 17
Compounds of the general formula I.3 where $R_n$ is 3-chloro, $R^d$ is hydrogen, and the combination of the index x and the group $R^x$ for any one compound corresponds to one line of Table A Table 18
Compounds of the general formula I.3 where $R_n$ is 3-chloro, $R^d$ is methyl, and the combination of the index x and the group $R^x$ for any one compound corresponds to one line of Table A Table 19
Compounds of the general formula 1.3 where $R_n$ is 3-chloro, $R^d$ is chlorine, and the combination of the index x and the group $R^x$ for any one compound corresponds to one line of Table A Table 20
Compounds of the general formula 1.3 where $R_n$ is 3-chloro, $R^d$ is methoxy, and the combination of the index x and the group $R^x$ for any one compound corresponds to one line of Table A

TABLE A

| No. | $R^x$ | X |
|---|---|---|
| 1 | H | O |
| 2 | 2-F | O |
| 3 | 3-F | O |
| 4 | 4-F | O |
| 5 | 2,4-$F_2$ | O |
| 6 | 2,4,6-$F_3$ | O |
| 7 | 2,3,4,5,6-$F_5$ | O |
| 8 | 2,3-$F_2$ | O |
| 9 | 2-Cl | 0 |
| 10 | 3-Cl | O |
| 11 | 4-Cl | O |
| 12 | 2,3-$Cl_2$ | O |
| 13 | 2,4-$Cl_2$ | O |
| 14 | 2,5-$Cl_2$ | O |
| 15 | 2,6-$Cl_2$ | O |
| 16 | 3,4-$Cl_2$ | O |

TABLE A-continued

| No. | $R^x$ | X |
|---|---|---|
| 17 | 3,5-$Cl_2$ | O |
| 18 | 2,3,4-$Cl_3$ | O |
| 19 | 2,3,5-$Cl_3$ | O |
| 20 | 2,3,6-$Cl_3$ | O |
| 21 | 2,4,5-$Cl_3$ | O |
| 22 | 2,4,6-$Cl_3$ | O |
| 23 | 3,4,5-$Cl_3$ | O |
| 24 | 2,3,4,6-$Cl_4$ | O |
| 25 | 2,3,5,6-$Cl_4$ | O |
| 26 | 2,3,4,5,6-$Cl_5$ | O |
| 27 | 2-Br | O |
| 28 | 3-Br | O |
| 29 | 4-Br | O |
| 30 | 2,4-$Br_2$ | O |
| 31 | 2,5-$Br_2$ | O |
| 32 | 2,6-$Br_2$ | O |
| 33 | 2,4,6-$Br_3$ | O |
| 34 | 2,3,4,5,6-$Br_5$ | O |
| 35 | 2-I | O |
| 36 | 3-I | O |
| 37 | 4-I | O |
| 38 | 2,4-$I_2$ | O |
| 39 | 2-Cl, 3-F | O |
| 40 | 2-Cl, 4-F | O |
| 41 | 2-Cl, 5-F | O |
| 42 | 2-Cl, 6-F | O |
| 43 | 2-Cl, 3-Br | O |
| 44 | 2-Cl, 4-Br | O |
| 45 | 2-Cl, 5-Br | O |
| 46 | 2-Cl, 6-Br | O |
| 47 | 2-Br, 3-Cl | O |
| 48 | 2-Br, 4-Cl | O |
| 49 | 2-Br, 5-Cl | O |
| 50 | 2-Br, 3-F | O |
| 51 | 2-Br, 4-F | O |
| 52 | 2-Br, 5-F | O |
| 53 | 2-Br, 6-F | O |
| 54 | 2-F, 3-Cl | O |
| 55 | 2-F, 4-Cl | O |
| 56 | 2-F, 5-Cl | O |
| 57 | 3-Cl, 4-F | O |
| 58 | 3-Cl, 5-F | O |
| 59 | 3-Cl, 4-Br | O |
| 60 | 3-Cl, 5-Br | O |
| 61 | 3-F, 4-Cl | O |
| 62 | 3-F, 4-Br | O |
| 63 | 3-Br, 4-Cl | O |
| 64 | 3-Br, 4-F | O |
| 65 | 2,6-$Cl_2$, 4-Br | O |
| 66 | 2-$CH_3$ | O |
| 67 | 3-$CH_3$ | O |
| 68 | 4-$CH_3$ | O |
| 69 | 2,3-$(CH_3)_2$ | O |
| 70 | 2,4-$(CH_3)_2$ | O |
| 71 | 2,5-$(CH_3)_2$ | O |
| 72 | 2,6-$(CH_3)_2$ | O |
| 73 | 3,4-$(CH_3)_2$ | O |
| 74 | 3,5-$(CH_3)_2$ | O |
| 75 | 2,3,5-$(CH_3)_3$ | O |
| 76 | 2,3,4-$(CH_3)_3$ | O |
| 77 | 2,3,6-$(CH_3)_3$ | O |
| 78 | 2,4,5-$(CH_3)_3$ | O |
| 79 | 2,4,6-$(CH_3)_3$ | O |
| 80 | 3,4,5-$(CH_3)_3$ | O |
| 81 | 2,3,4,6-$(CH_3)_4$ | O |
| 82 | 2,3,5,6-$(CH_3)_4$ | O |
| 83 | 2,3,4,5,6-$(CH_3)_5$ | O |
| 84 | 2-$C_2H_5$ | O |
| 85 | 3-$C_2H_5$ | O |
| 86 | 4-$C_2H_5$ | O |
| 87 | 2,4-$(C_2H_5)_5$ | O |
| 88 | 2,6-$(C_2H_5)_2$ | O |
| 89 | 3,5-$(C_2H_5)_2$ | O |
| 90 | 2,4,6-$(C_2H_5)_3$ | O |
| 91 | 2-n-$C_3H_7$ | O |
| 92 | 3-n-$C_3H_7$ | O |
| 93 | 4-n-$C_3H_7$ | O |

TABLE A-continued

| No. | R$^x$ | X |
|---|---|---|
| 94 | 2-i-C$_3$H$_7$ | O |
| 95 | 3-i-C$_3$H$_7$ | O |
| 96 | 4-i-C$_3$H$_7$ | O |
| 97 | 2,4-(i-C$_3$H$_7$)$_2$ | O |
| 98 | 2,6-(i-C$_3$H$_7$)$_2$ | O |
| 99 | 3,5-(i-C$_3$H$_7$)$_2$ | O |
| 100 | 2-s-C$_4$H$_9$ | O |
| 101 | 3-s-C$_4$H$_9$ | O |
| 102 | 4-s-C$_4$H$_9$ | O |
| 103 | 2-t-C$_4$H$_9$ | O |
| 104 | 3-t-C$_4$H$_9$ | O |
| 105 | 4-t-C$_4$H$_9$ | O |
| 106 | 4-n-C$_9$H$_{19}$ | O |
| 107 | 2-CH$_3$, 4-t-C$_4$H$_9$ | O |
| 108 | 2-CH$_3$, 6-t-C$_4$H$_9$ | O |
| 109 | 2-CH$_3$, 4-i-C$_3$H$_7$ | O |
| 110 | 2-CH$_3$, 5-i-C$_3$H$_7$ | O |
| 111 | 3-CH$_3$, 4-i-C$_3$H$_7$ | O |
| 112 | 2-cyclo-C$_6$H$_{11}$ | O |
| 113 | 3-cyclo-C$_6$H$_{11}$ | O |
| 114 | 4-cyclo-C$_6$H$_{11}$ | O |
| 115 | 2-Cl, 4-C$_6$H$_5$ | O |
| 116 | 2-Br, 4-C$_6$H$_5$ | O |
| 117 | 2-OCH$_3$ | O |
| 118 | 3-OCH$_3$ | O |
| 119 | 4-OCH$_3$ | O |
| 120 | 2-OC$_2$H$_5$ | O |
| 121 | 3-O-C$_2$H$_5$ | O |
| 122 | 4-O-C$_2$H$_5$ | O |
| 123 | 2-O-n-C$_3$H$_7$ | O |
| 124 | 3-O-n-C$_3$H$_7$ | O |
| 125 | 4-O-n-C$_3$H$_7$ | O |
| 126 | 2-O-i-C$_3$H$_7$ | O |
| 127 | 3-O-i-C$_3$H$_7$ | O |
| 128 | 4-O-i-C$_3$H$_7$ | O |
| 129 | 2-O-n-C$_6$H$_{13}$ | O |
| 130 | 3-O-n-C$_6$H$_{13}$ | O |
| 131 | 4-O-n-C$_6$H$_{13}$ | O |
| 132 | 2-O-CH$_2$C$_6$H$_5$ | O |
| 133 | 3-O-CH$_2$C$_6$H$_5$ | O |
| 134 | 4-O-CH$_2$C$_6$H$_5$ | O |
| 135 | 2-O-(CH$_2$)$_3$C$_6$H$_5$ | O |
| 136 | 4-O-(CH$_2$)$_3$C$_6$H$_5$ | O |
| 137 | 2,3-(OCH$_3$)$_2$ | O |
| 138 | 2,4-(OCH$_3$)$_2$ | O |
| 139 | 2,5-(OCH$_3$)$_2$ | O |
| 140 | 2,6-(OCH$_3$)$_2$ | O |
| 141 | 3,4-(OCH$_3$)$_2$ | O |
| 142 | 3,5-(OCH$_3$)$_2$ | O |
| 143 | 2-O-t-C$_4$H$_9$ | O |
| 144 | 3-O-t-C$_4$H$_9$ | O |
| 145 | 4-O-t-C$_4$H$_9$ | O |
| 146 | 3-(3'-Cl—C$_6$H$_4$) | O |
| 147 | 4-(4'-CH$_3$—C$_6$H$_4$) | O |
| 148 | 2-O-C$_6$H$_5$ | O |
| 149 | 3-O-C$_6$H$_5$ | O |
| 150 | 4-O-C$_6$H$_5$ | O |
| 151 | 2-O-(2'-F—C$_6$H$_4$) | O |
| 152 | 3-O-(3'-Cl—C$_6$H$_4$) | O |
| 153 | 4-O-(4'-CH$_3$—C$_6$H$_4$) | O |
| 154 | 2,3,6-(CH$_3$)$_3$, 4-F | O |
| 155 | 2,3,6-(CH$_3$)$_3$, 4-Cl | O |
| 156 | 2,3,6-(CH$_3$)$_3$, 4-Br | O |
| 157 | 2,4-(CH$_3$)$_2$, 6-F | O |
| 158 | 2,4-(CH$_3$)$_2$, 6-Cl | O |
| 159 | 2,4-(CH$_3$)$_2$, 6-Br | O |
| 160 | 2-i-C$_3$H$_7$, 4-Cl, 5-CH$_3$ | O |
| 161 | 2-Cl, 4-NO$_2$ | O |
| 162 | 2-NO$_2$, 4-Cl | O |
| 163 | 2-OCH$_3$, 5-NO$_2$ | O |
| 164 | 2,4-Cl$_2$, 5-NO$_2$ | O |
| 165 | 2,4-Cl$_2$, 6-NO$_2$ | O |
| 166 | 2,6-Cl$_2$, 4-NO$_2$ | O |
| 167 | 2,6-Br$_2$, 4-NO$_2$ | O |
| 168 | 2,6-I$_2$, 4-NO$_2$ | O |
| 169 | 2-CH$_3$, 5-i-C$_3$H$_7$, 4-Cl | O |
| 170 | 2-CO$_2$CH$_3$ | O |
| 171 | 3-CO$_2$CH$_3$ | O |
| 172 | 4-CO$_2$CH$_3$ | O |
| 173 | 2-CH$_2$—OCH$_3$ | O |
| 174 | 3-CH$_2$—OCH$_3$ | O |
| 175 | 4-CH$_2$—OCH$_3$ | O |
| 176 | 2-Me-4-CH$_3$—CH(CH$_3$)—CO | O |
| 177 | 2-CH$_3$-4-(CH$_3$—C=NOCH$_3$) | O |
| 178 | 2-CH$_3$-4-(CH$_3$—C=NOC$_2$H$_5$) | O |
| 179 | 2-CH$_3$-4-(CH$_3$—C=NO-n-C$_3$H$_7$) | O |
| 180 | 2-CH$_3$-4-(CH$_3$—C=NO-i-C$_3$H$_7$) | O |
| 181 | 2,5-(CH$_3$)$_2$-4-(CH$_3$—C=NOCH$_3$) | O |
| 182 | 2,5-(CH$_3$)$_2$-4-(CH$_3$—C=NOC$_2$H$_5$) | O |
| 183 | 2,5-(CH$_3$)$_2$-4-(CH$_3$—C=NO-n-C$_3$H$_7$) | O |
| 184 | 2,5-(CH$_3$)$_2$-4-(CH$_3$—C=NO-i-C$_3$H$_7$) | O |
| 185 | 2-C$_6$H$_5$ | O |
| 186 | 3-C$_6$H$_5$ | O |
| 187 | 4-C$_6$H$_5$ | O |
| 188 | 2-(2'-F—C$_6$H$_4$) | O |
| 189 | 2-CH$_3$, 5-Br | O |
| 190 | 2-CH$_3$, 6-Br | O |
| 191 | 2-Cl, 3-CH$_3$ | O |
| 192 | 2-Cl, 4-CH$_3$ | O |
| 193 | 2-Cl, 5-CH$_3$ | O |
| 194 | 2-F, 3-CH$_3$ | O |
| 195 | 2-F, 4-CH$_3$ | O |
| 196 | 2-F, 5-CH$_3$ | O |
| 197 | 2-Br, 3-CH$_3$ | O |
| 198 | 2-Br, 4-CH$_3$ | O |
| 199 | 2-Br, 5-CH$_3$ | O |
| 200 | 3-CH$_3$, 4-Cl | O |
| 201 | 3-CH$_3$, 5-Cl | O |
| 202 | 3-CH$_3$, 4-F | O |
| 203 | 3-CH$_3$, 5-F | O |
| 204 | 3-CH$_3$, 4-Br | O |
| 205 | 3-CH$_3$, 5-Br | O |
| 206 | 3-F, 4-CH$_3$ | O |
| 207 | 3-Cl, 4-CH$_3$ | O |
| 208 | 3-Br, 4-CH$_3$ | O |
| 209 | 2-Cl, 4,5-(CH$_3$)$_2$ | O |
| 210 | 2-Br, 4,5-(CH$_3$)$_2$ | O |
| 211 | 2-Cl, 3,5-(CH$_3$)$_2$ | O |
| 212 | 2-Br, 3,5-(CH$_3$)$_2$ | O |
| 213 | 2,6-Cl$_2$, 4-CH$_3$ | O |
| 214 | 2,6-F$_2$, 4-CH$_3$ | O |
| 215 | 2,6-Br$_2$, 4-CH$_3$ | O |
| 216 | 2,4-Br$_2$, 6-CH$_3$ | O |
| 217 | 2,4-F$_2$, 6-CH$_3$ | O |
| 218 | 2,4-Br$_2$, 6-CH$_3$ | O |
| 219 | 2,6-(CH$_3$)$_2$, 4-F | O |
| 220 | 2,6-(CH$_3$)$_2$, 4-Cl | O |
| 221 | 2,6-(CH$_3$)$_2$, 4-Br | O |
| 222 | 3,5-(CH$_3$)$_2$, 4-F | O |
| 223 | 3,5-(CH$_3$)$_2$, 4-Cl | O |
| 224 | 3,5-(CH$_3$)$_2$, 4-Br | O |
| 225 | 2-CF$_3$ | O |
| 226 | 3-CF$_3$ | O |
| 227 | 4-CF$_3$ | O |
| 228 | 2-OCF$_3$ | O |
| 229 | 3-OCF$_3$ | O |
| 230 | 4-OCF$_3$ | O |
| 231 | 3-OCH$_2$CHF$_2$ | O |
| 232 | 2-NO$_2$ | O |
| 233 | 3-NO$_2$ | O |
| 234 | 4-NO$_2$ | O |
| 235 | 2-CN | O |
| 236 | 3-CN | O |
| 237 | 4-CN | O |
| 238 | 2-CH$_3$, 3-Cl | O |
| 239 | 2-CH$_3$, 4-Cl | O |
| 240 | 2-CH$_3$, 5-Cl | O |
| 241 | 2-CH$_3$, 6-Cl | O |
| 242 | 2-CH$_3$, 3-F | O |
| 243 | 2-CH$_3$, 4-F | O |
| 244 | 2-CH$_3$, 5-F | O |
| 245 | 2-CH$_3$, 6-F | O |
| 246 | 2-CH$_3$, 3-Br | O |
| 247 | 2-CH$_3$, 4-Br | O |

TABLE A-continued

| No. | $R^X$ | X |
|---|---|---|
| 248 | 2,5-$F_2$ | O |
| 249 | 2,6-$F_2$ | O |
| 250 | 3,4-$F_2$ | O |
| 251 | 3,5-$F_2$ | O |
| 252 | H | 1 |
| 253 | 2-F | 1 |
| 254 | 3-F | 1 |
| 255 | 4-F | 1 |
| 256 | 2,4-$F_2$ | 1 |
| 257 | 2,4,6-$F_3$ | 1 |
| 258 | 2,3,4,5,6-$F_5$ | 1 |
| 259 | 2,3-$F_2$ | 1 |
| 260 | 2-Cl | 1 |
| 261 | 3-Cl | 1 |
| 262 | 4-Cl | 1 |
| 263 | 2,3-$Cl_2$ | 1 |
| 264 | 2,4-$Cl_2$ | 1 |
| 265 | 2,5-$Cl_2$ | 1 |
| 266 | 2,6-$Cl_2$ | 1 |
| 267 | 3,4-$Cl_2$ | 1 |
| 268 | 3,5-$Cl_2$ | 1 |
| 269 | 2,3,4-$Cl_3$ | 1 |
| 270 | 2,3,5-$Cl_3$ | 1 |
| 271 | 2,3,6-$Cl_3$ | 1 |
| 272 | 2,4,5-$Cl_3$ | 1 |
| 273 | 2,4,6-$Cl_3$ | 1 |
| 274 | 3,4,5-$Cl_3$ | 1 |
| 275 | 2,3,4,6-$Cl_4$ | 1 |
| 276 | 2,3,5,6-$Cl_4$ | 1 |
| 277 | 2,3,4,5,6-$Cl_5$ | 1 |
| 278 | 2-Br | 1 |
| 279 | 3-Br | 1 |
| 280 | 4-Br | 1 |
| 281 | 2,4-$Br_2$ | 1 |
| 282 | 2,5-$Br_2$ | 1 |
| 283 | 2,6-$Br_2$ | 1 |
| 284 | 2,4,6-$Br_3$ | 1 |
| 285 | 2,3,4,5,6-$Br_5$ | 1 |
| 286 | 2-I | 1 |
| 287 | 3-I | 1 |
| 288 | 4-I | 1 |
| 289 | 2,4-$I_2$ | 1 |
| 290 | 2-Cl, 3-F | 1 |
| 291 | 2-Cl, 4-F | 1 |
| 292 | 2-Cl, 5-F | 1 |
| 293 | 2-Cl, 6-F | 1 |
| 294 | 2-Cl, 3-Br | 1 |
| 295 | 2-Cl, 4-Br | 1 |
| 296 | 2-Cl, 5-Br | 1 |
| 297 | 2-Cl, 6-Br | 1 |
| 298 | 2-Br, 3-Cl | 1 |
| 299 | 2-Br, 4-Cl | 1 |
| 300 | 2-Br, 5-Cl | 1 |
| 301 | 2-Br, 3-F | 1 |
| 302 | 2-Br, 4-F | 1 |
| 303 | 2-Br, 5-F | 1 |
| 304 | 2-Br, 6-F | 1 |
| 305 | 2-F, 3-Cl | 1 |
| 306 | 2-F, 4-Cl | 1 |
| 307 | 2-F, 5-Cl | 1 |
| 308 | 3-Cl, 4-F | 1 |
| 309 | 3-Cl, 5-F | 1 |
| 310 | 3-Cl, 4-Br | 1 |
| 311 | 3-Cl, 5-Br | 1 |
| 312 | 3-F, 4-Cl | 1 |
| 313 | 3-F, 4-Br | 1 |
| 314 | 3-Br, 4-Cl | 1 |
| 315 | 3-Br, 4-F | 1 |
| 316 | 2,6-$Cl_2$, 4-Br | 1 |
| 317 | 2-$CH_3$ | 1 |
| 318 | 3-$CH_3$ | 1 |
| 319 | 4-$CH_3$ | 1 |
| 320 | 2,3-$(CH_3)_2$ | 1 |
| 321 | 2,4-$(CH_3)_2$ | 1 |
| 322 | 2,5-$(CH_3)_2$ | 1 |
| 323 | 2,6-$(CH_3)_2$ | 1 |
| 324 | 3,4-$(CH_3)_2$ | 1 |
| 325 | 3,5-$(CH_3)_2$ | 1 |
| 326 | 2,3,5-$(CH_3)_3$ | 1 |
| 327 | 2,3,4-$(CH_3)_3$ | 1 |
| 328 | 2,3,6-$(CH_3)_3$ | 1 |
| 329 | 2,4,5-$(CH_3)_3$ | 1 |
| 330 | 2,4,6-$(CH_3)_3$ | 1 |
| 331 | 3,4,5-$(CH_3)_3$ | 1 |
| 332 | 2,3,4,6-$(CH_3)_4$ | 1 |
| 333 | 2,3,5,6-$(CH_3)_4$ | 1 |
| 334 | 2,3,4,5,6-$(CH_3)_5$ | 1 |
| 335 | 2-$C_2H_5$ | 1 |
| 336 | 3-$C_2H_5$ | 1 |
| 337 | 4-$C_2H_5$ | 1 |
| 338 | 2,4-$(C_2H_5)_5$ | 1 |
| 339 | 2,6-$(C_2H_5)_2$ | 1 |
| 340 | 3,5-$(C_2H_5)_2$ | 1 |
| 341 | 2,4,6-$(C_2H_5)_3$ | 1 |
| 342 | 2-n-$C_3H_7$ | 1 |
| 343 | 3-n-$C_3H_7$ | 1 |
| 344 | 4-n-$C_3H_7$ | 1 |
| 345 | 2-i-$C_3H_7$ | 1 |
| 346 | 3-i-$C_3H_7$ | 1 |
| 347 | 4-i-$C_3H_7$ | 1 |
| 348 | 2,4-(i-$C_3H_7)_2$ | 1 |
| 349 | 2,6-(i-$C_3H_7)_2$ | 1 |
| 350 | 3,5-(i-$C_3H_7)_2$ | 1 |
| 351 | 2-s-$C_4H_9$ | 1 |
| 352 | 3-s-$C_4H_9$ | 1 |
| 353 | 4-s-$C_4H_9$ | 1 |
| 354 | 2-t-$C_4H_9$ | 1 |
| 355 | 3-t-$C_4H_9$ | 1 |
| 356 | 4-t-$C_4H_9$ | 1 |
| 357 | 4-n-$C_9H_{19}$ | 1 |
| 358 | 2-$CH_3$, 4-t-$C_4H_9$ | 1 |
| 359 | 2-$CH_3$, 6-t-$C_4H_9$ | 1 |
| 360 | 2-$CH_3$, 4-i-$C_3H_7$ | 1 |
| 361 | 2-$CH_3$, 5-i-$C_3H_7$ | 1 |
| 362 | 3-$CH_3$, 4-i-$C_3H_7$ | 1 |
| 363 | 2-cyclo-$C_6H_{11}$ | 1 |
| 364 | 3-cyclo-$C_6H_{11}$ | 1 |
| 365 | 4-cyclo-$C_6H_{11}$ | 1 |
| 366 | 2-Cl, 4-$C_6H_5$ | 1 |
| 367 | 2-Br, 4-$C_6H_5$ | 1 |
| 368 | 2-$OCH_3$ | 1 |
| 369 | 3-$OCH_3$ | 1 |
| 370 | 4-$OCH_3$ | 1 |
| 371 | 2-$OC_2H_5$ | 1 |
| 372 | 3-O—$C_2H_5$ | 1 |
| 373 | 4-O—$C_2H_5$ | 1 |
| 374 | 2-O-n-$C_3H_7$ | 1 |
| 375 | 3-O-n-$C_3H_7$ | 1 |
| 376 | 4-O-n-$C_3H_7$ | 1 |
| 377 | 2-O-i-$C_3H_7$ | 1 |
| 378 | 3-O-i-$C_3H_7$ | 1 |
| 379 | 4-O-i-$C_3H_7$ | 1 |
| 380 | 2-O-n-$C_6H_{13}$ | 1 |
| 381 | 3-O-n-$C_6H_{13}$ | 1 |
| 382 | 4-O-n-$C_6H_{13}$ | 1 |
| 383 | 2-O—$CH_2C_6H_5$ | 1 |
| 384 | 3-O—$CH_2C_6H_5$ | 1 |
| 385 | 4-O—$CH_2C_6H_5$ | 1 |
| 386 | 2-O—$(CH_2)_3C_6H_5$ | 1 |
| 387 | 4-O—$(CH_2)_3C_6H_5$ | 1 |
| 388 | 2,3-$(OCH_3)_2$ | 1 |
| 389 | 2,4-$(OCH_3)_2$ | 1 |
| 390 | 2,5-$(OCH_3)_2$ | 1 |
| 391 | 2,6-$(OCH_3)_2$ | 1 |
| 392 | 3,4-$(OCH_3)_2$ | 1 |
| 393 | 3,5-$(OCH_3)_2$ | 1 |
| 394 | 2-O-t-$C_4H_9$ | 1 |
| 395 | 3-O-t-$C_4H_9$ | 1 |
| 396 | 4-O-t-$C_4H_9$ | 1 |
| 397 | 3-(3'-Cl—$C_6H_4$) | 1 |
| 398 | 4-(4'-$CH_3$—$C_6H_4$) | 1 |
| 399 | 2-O—$C_6H_5$ | 1 |
| 400 | 3-O—$C_6H_5$ | 1 |
| 401 | 4-O—$C_6H_5$ | 1 |

TABLE A-continued

| No. | R$^X$ | X |
|---|---|---|
| 402 | 2-O—(2'-F—C$_6$H$_4$) | 1 |
| 403 | 3-O-(3'-Cl—C$_6$H$_4$) | 1 |
| 404 | 4-O-(4'-CH$_3$—C$_6$H$_4$) | 1 |
| 405 | 2,3,6-(CH$_3$)$_3$, 4-F | 1 |
| 406 | 2,3,6-(CH$_3$)$_3$, 4-Cl | 1 |
| 407 | 2,3,6-(CH$_3$)$_3$, 4-Br | 1 |
| 408 | 2,4-(CH$_3$)$_2$, 6-F | 1 |
| 409 | 2,4-(CH$_3$)$_2$, 6-Cl | 1 |
| 410 | 2,4-(CH$_3$)$_2$, 6-Br | 1 |
| 411 | 2-i-C$_3$H$_7$, 4-Cl, 5-CH$_3$ | 1 |
| 412 | 2-Cl, 4-NO$_2$ | 1 |
| 413 | 2-NO$_2$, 4-Cl | 1 |
| 414 | 2-OCH$_3$, 5-NO$_2$ | 1 |
| 415 | 2,4-Cl$_2$, 5-NO$_2$ | 1 |
| 416 | 2,4-Cl$_2$, 6-NO$_2$ | 1 |
| 417 | 2,6-Cl$_2$, 4-NO$_2$ | 1 |
| 418 | 2,6-Br$_2$, 4-NO$_2$ | 1 |
| 419 | 2,6-I$_2$, 4-NO$_2$ | 1 |
| 420 | 2-CH$_3$, 5-i-C$_3$H$_7$, 4-Cl | 1 |
| 421 | 2-CO$_2$CH$_3$ | 1 |
| 422 | 3-CO$_2$CH$_3$ | 1 |
| 423 | 4-CO$_2$CH$_3$ | 1 |
| 424 | 2-CH$_2$—OCH$_3$ | 1 |
| 425 | 3-CH$_2$—OCH$_3$ | 1 |
| 426 | 4-CH$_2$—OCH$_3$ | 1 |
| 427 | 2-Me-4-CH$_3$—CH(CH$_3$)—CO | 1 |
| 428 | 2-CH$_3$-4-(CH$_3$—C=NOCH$_3$) | 1 |
| 429 | 2-CH$_3$-4-(CH$_3$—C=NOC$_2$H$_5$) | 1 |
| 430 | 2-CH$_3$-4-(CH$_3$—C=NO-n-C$_3$H$_7$) | 1 |
| 431 | 2-CH$_3$-4-(CH$_3$—C=NO-i-C$_3$H$_7$) | 1 |
| 432 | 2,5-(CH$_3$)$_2$-4-(CH$_3$—C=NOCH$_3$) | 1 |
| 433 | 2,5-(CH$_3$)$_2$-4-(CH$_3$—C=NOC$_2$H$_5$) | 1 |
| 434 | 2,5-(CH$_3$-4-(CH$_3$—C=NO-n-C$_3$H$_7$) | 1 |
| 435 | 2,5-(CH$_3$)$_2$-4-(CH$_3$—C=NO-i-C$_3$H$_7$) | 1 |
| 436 | 2-C$_6$H$_5$ | 1 |
| 437 | 3-C$_6$H$_5$ | 1 |
| 438 | 4-C$_6$H$_5$ | 1 |
| 439 | 2-(2'-F-C$_6$H$_4$) | 1 |
| 440 | 2-CH$_3$, 5-Br | 1 |
| 441 | 2-CH$_3$, 6-Br | 1 |
| 442 | 2-Cl, 3-CH$_3$ | 1 |
| 443 | 2-Cl, 4-CH$_3$ | 1 |
| 444 | 2-Cl, 5-CH$_3$ | 1 |
| 445 | 2-F, 3-CH$_3$ | 1 |
| 446 | 2-F, 4-CH$_3$ | 1 |
| 447 | 2-F, 5-CH$_3$ | 1 |
| 448 | 2-Br, 3-CH$_3$ | 1 |
| 449 | 2-Br, 4-CH$_3$ | 1 |
| 450 | 2-Br, 5-CH$_3$ | 1 |
| 451 | 3-CH$_3$, 4-Cl | 1 |
| 452 | 3-CH$_3$, 5-Cl | 1 |
| 453 | 3-CH$_3$, 4-F | 1 |
| 454 | 3-CH$_3$, 5-F | 1 |
| 455 | 3-CH$_3$, 4-Br | 1 |
| 456 | 3-CH$_3$, 5-Br | 1 |
| 457 | 3-F, 4-CH$_3$ | 1 |
| 458 | 3-Cl, 4-CH$_3$ | 1 |
| 459 | 3-Br, 4-CH$_3$ | 1 |
| 460 | 2-Cl, 4,5-(CH$_3$)$_2$ | 1 |
| 461 | 2-Br, 4,5-(CH$_3$)$_2$ | 1 |
| 462 | 2-Cl, 3,5-(CH$_3$)$_2$ | 1 |
| 463 | 2-Br, 3,5-(CH$_3$)$_2$ | 1 |
| 464 | 2,6-Cl$_2$, 4-CH$_3$ | 1 |
| 465 | 2,6-F$_2$, 4-CH$_3$ | 1 |
| 466 | 2,6-Br$_2$, 4-CH$_3$ | 1 |
| 467 | 2,4-Br$_2$, 6-CH$_3$ | 1 |
| 468 | 2,4-F$_2$, 6-CH$_3$ | 1 |
| 469 | 2,4-Br$_2$, 6-CH$_3$ | 1 |
| 470 | 2,6-(CH$_3$)$_2$, 4-F | 1 |
| 471 | 2,6-(CH$_3$)$_2$, 4-Cl | 1 |
| 472 | 2,6-(CH$_3$)$_2$, 4-Br | 1 |
| 473 | 3,5-(CH$_3$)$_2$, 4-F | 1 |
| 474 | 3,5-(CH$_3$)$_2$, 4-Cl | 1 |
| 475 | 3,5-(CH$_3$)$_2$, 4-Br | 1 |
| 476 | 2-CF$_3$ | 1 |
| 477 | 3-CF$_3$ | 1 |
| 478 | 4-CF$_3$ | 1 |
| 479 | 2-OCF$_3$ | 1 |
| 480 | 3-OCF$_3$ | 1 |
| 481 | 4-OCF$_3$ | 1 |
| 482 | 3-OCH$_2$CHF$_2$ | 1 |
| 483 | 2-NO$_2$ | 1 |
| 484 | 3-NO$_2$ | 1 |
| 485 | 4-NO$_2$ | 1 |
| 486 | 2-CN | 1 |
| 487 | 3-CN | 1 |
| 488 | 4-CN | 1 |
| 489 | 2-CH$_3$, 3-Cl | 1 |
| 490 | 2-CH$_3$, 4-Cl | 1 |
| 491 | 2-CH$_3$, 5-Cl | 1 |
| 492 | 2-CH$_3$, 6-Cl | 1 |
| 493 | 2-CH$_3$, 3-F | 1 |
| 494 | 2-CH$_3$, 4-F | 1 |
| 495 | 2-CH$_3$, 5-F | 1 |
| 496 | 2-CH$_3$, 6-F | 1 |
| 497 | 2-CH$_3$, 3-Br | 1 |
| 498 | 2-CH$_3$, 4-Br | 1 |
| 499 | 2,5-F$_2$ | 1 |
| 500 | 2,6-F$_2$ | 1 |
| 501 | 3,4-F$_2$ | 1 |
| 502 | 3,5-F$_2$ | 1 |

The compounds of the formula I according to the invention are suitable for controlling fungal pests and animal pests from the classes of the insects, arachnids and nematodes. They can be employed as fungicides and pesticides in crop protection, but also in the hygiene, stored-product and veterinary sectors.

The harmful insects include:
from the order of the lepidopterans (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula andalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis,*
furthermore *Galleria mellonella* and *Sitotroga cerealella, Ephestia cautella, Tineola bisselliella;* from the order of the beetles (Coleoptera), for example, Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, furthermore Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;

from the order of the dipterans (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa, furthermore Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;

from the order of the thrips (Thysanoptera), for example, Frankliniella fusca, Frankliniella occidentalis, Frankliniella tritici, Haplothrips tritici, Scirtothrips citri, Thrips oryzae, Thrips palmi, Thrips tabaci;

from the order of the hymenopterans (Hymenoptera), for example, Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the homopterans (Homoptera), for example, Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;

from the order of the termites (Isoptera), for example, Calotermes flavicollis, Leucotermes flavipes, Macrotermes subhyalinus, Odontotermes formosanus, Reticulitermes lucifugus, Termes natalensis;

from the order of the orthopterans (Orthoptera), for example, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, furthermore Acheta domestica, Blatta orientalis, Blattella germanica, Periplaneta americana;

from the order of the Arachnoidea, for example, phytophagous mites, such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae, ticks, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus and Rhipicephalus evertsi, and also animal-parasitic mites, such as Dermanyssus gallinae, Psoroptes ovis and Sarcoptes scabiei;

from the class of the nematodes, for example, root knot nematodes, eg. Meloidogyne hapla, Meloidogyne incognita, Meloidogyne javanica, cyst nematodes, eg. Globodera pallida, Globodera rostochiensis, Heterodera avenae, Heterodera glycines, Heterodera schachtii, migratory endoparasites and semi-endoparasitic nematodes, eg. Heliocotylenchus multicinctus, Hirschmanniella oryzae, Hoplolaimus spp, Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans, stem eel worms and folia nematodes, eg. Anguina tritici, Aphelenchoides besseyi, Ditylenchus angustus, Ditylenchus dipsaci, virus vectors, eg. Longidorus spp, Trichodorus christei, Trichodorus viruliferus, Xiphinema index, Xiphinema mediterraneum.

The active ingredients can be used as such, in the form of their formulations or in the form of the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended use; in any case, they should guarantee the finest possible distribution of the active ingredients according to the invention.

When used as fungicides, some of the compounds of the formula I have a systemic action. They can be employed as foliar- and soil-acting fungicides against a broad spectrum of phytopathogenic fungi, in particular from the classes of the Ascomycetes, Deuteromycetes, Phycomycetes and Basidiomycetes.

They are particularly important for controlling a large number of fungi which infect a variety of crop plants, such as wheat, rye, barley, oats, rice, maize, lawn, cotton, soya beans, coffee, sugar cane, grape vines, fruit species, ornamentals and vegetable species, such as cucumbers, beans and cucurbits, as well as the seeds of these plants.

Specifically, the compounds I are suitable for controlling the following plant diseases:

*Erysiphe graminis* (powdery mildew) in cereals,

*Erysiphe cichoracearum* and *Sphaerotheca fuliginea* in cucurbits,

*Podosphaera leucotricha* in apples,

Uncinula necator in grape vines,

Puccinia species in cereals,

Rhizoctonia species in cotton and lawn,

Ustilago species in cereals and sugar cane,

*Venturia inaequalis* (scab) in apples,

Helminthosporium species in cereals,

*Septoria nodorum* in wheat,

*Botrytis cinerea* (gray mold) in strawberries and grape vines,

*Cercospora arachidicola* in groundnuts,

*Pseudocercosporella herpotrichoides* in wheat, barley,

*Pyricularia oryzae* in rice,

Phytophthora infestans in potatoes and tomatoes,

Fusarium and Verticillium species in a variety of plants,

*Plasmopara viticola* in grape vines,

Alternaria species in vegetables and fruit.

The novel compounds can also be employed in the protection of materials (wood), eg. against *Paecilomyces variotii*.

They can be converted into the customary formulations, such as solutions, emulsions, suspensions, dusts, powders, pastes or granules. The use forms depend on the specific intended purpose; in any case, they should guarantee the finest possible distribution of the active ingredients.

The formulations are prepared in a known manner, eg. by extending the active ingredient with solvents and/or carriers, if desired using emulsifiers and dispersants, it also being possible to use other organic solvents as auxiliary solvents if water is used as the diluent.

Suitable auxiliaries are essentially the following:

solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water;

carriers, such as ground natural minerals (eg. kaolins, clays, talc, chalk) and ground synthetic minerals (eg. highly-disperse silica, silicates);

emulsifiers, such as nonionic and anionic emulsifiers (eg. polyoxyethylene fatty alcohol ethers, alkylsulfonates and arylsulfonates), and dispersants, such as lignosulfite waste liquors and methylcellulose.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ether, condensation products of sulfonated naphthalene and its derivatives with formaldehyde, condensation products of naphthalene, or the naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Aqueous use forms can be prepared from emulsion concentrates, dispersions, pastes, wettable powders or water-dispersible granules by adding water. To prepare emulsions, pastes or oil dispersions, substrates as such, or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, which are suitable for dilution with water.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers.

Solid carriers are mineral earths, such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powder or other solid carriers.

The active ingredient concentrations in the ready-to-use preparations can be varied within substantial ranges.

Quite generally, the compositions comprise from 0.0001 to 95% by weight of active ingredient.

Formulations comprising more than 95% by weight of active ingredient can successfully be applied by the ulrta-low-volume method (ULV), it even being possible to use the active ingredient without additives.

For use as fungicides, concentrations from 0.01 to 95% by weight, preferably from 0.5 to 90% by weight, of active ingredient are recommended. Suitable for use as insecticides are formulations comprising 0.0001 to 10% by weight, preferably 0.01 to 1% by weight, of active ingredient.

The active ingredients are usually employed in a purity of 90% to 100%, preferably 95% to 100% (according to NMR spectrum).

Examples of such preparations are:

I. a solution of 90 parts by weight of a compound I according to the invention and 10 parts by weight of N-methyl-α-pyrrolidone, which is suitable for use in the form of microdrops;

II. a solution of 20 parts by weight of a compound I according to the invention in a mixture of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the formulation in water;

III. a solution of 20 parts by weight of a compound I according to the invention in a mixture of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil; a dispersion is obtained by finely distributing the formulation in water;

IV. an aqueous dispersion of 20 parts by weight of a compound I according to the invention in a mixture of 25 parts by weight of cyclohexanone, 65 parts by weight of a mineral oil fraction of boiling point 210 to 280° C. and 10 parts by weight of the adduct of 40 mol of ethylene oxide to 1 mol of castor oil; a dispersion is obtained by finely distributing the formulation in water;

V. a mixture, ground in a hammer mill, of 20 parts by weight of a compound I according to the invention, 3 parts by weight of sodium diisobutylnaphthalene-α-sulfonate, 17 parts by weight of a sodium lignosulfonate from a sulfite waste liquor and 60 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil, which was sprayed onto the surface of this silica gel; this preparation imparts good adhesion properties to the active ingredient;

VIII. a stable aqueous dispersion of 40 parts by weight of a compound I according to the invention, 10 parts by weight of the sodium salt of a phenosulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of sodium diisobutylnaphthalene-α-sulfonate, 20 parts by weight of a sodium lignosulfonate from a sulfite waste liquor, 38 parts by weight of silica gel and 38 parts by weight of kaolin. By finely distributing the mixture in 10,000 parts by weight of water, a spray mixture comprising 0.1% by weight of the active ingredient is obtained.

The compounds I are used by treating the fungi, or the seeds, plants, materials or the soil to be protected against fungal infection, with a fungicidally active amount of the active ingredients.

Application is effected before or after infection of the materials, plants or seeds with the fungi.

Depending on the nature of the desired effect, the application rates are from 0.02 to 3 kg of active ingredient per ha, preferably 0.1 to 1 kg/ha.

In the treatment of seed, amounts of active ingredient of from 0.001 to 50 g, preferably from 0.01 to 10 g, are generally required per kilogram of seed.

Under open conditions, the application rate of active ingredient for the control of pests is from 0.02 to 10, preferably 0.1 to 2.0, kg/ha of active ingredient.

The compounds I, alone or in combination with herbicides or fungicides, can also be applied together with other crop protection products, as a mixture, for example with growth regulators or with pesticides or bactericides. Also of interest is the miscibility with fertilizers or with mineral salt solutions, which are employed for alleviating nutrient and trace element deficiencies.

The crop protection products and fertilizers can be added to the compositions according to the invention in a ratio by weight of 1:10 to 10:1, if desired also immediately prior to use (tank mix). In many cases, mixing them with fungicides or insecticides results in a widened fungicidal spectrum of action.

The following list of fungicides, together with which the compounds according to the invention can be used, is intended to illustrate the possible combinations, but not by way of limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide; nitro derivatives, such as dinitro(1-methylheptyl)phenyl crotonate, 2-sec-butyl-4,6-dinitrophenyl-3,3-dimethyl acrylate, 2-sec-butyl-4, 6-dinitrophenyl isopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis-(dimethylamino)-phosphinyl]-3-phenyl-1,2,4-triazole, 2,3-dicyano-1,4-dithio-anthraquinone, 2-thio-1,3-dithiolo-β-[4,5-b] quinoxaline, methyl 1-(butylcarbamoyl)-2-benzimidazolecarbamate, 2-methoxycarbonylamino-benzimidazole, 2-(furyl-(2))-benzimidazole, 2-(thiazolyl-(4))-benzimidazole, N-(1,1,2,2-tetrachloroethylthio)-tetrahydrophthalimide, N-trichloromethylthio-tetrahydrophthalimide, N-trichloromethylthio-phthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2, 5-dimethoxybenzene, 4-(2-chlorophenylhydrazono)-3-methyl-5-isoxazolone, pyridine 2-thio-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3- carboxanilide, 2,4,5-trimethylfuran-3-carboxanilide, 2,5-dimethylfuran-3-carbo-cyclohexyl-amide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-(1-(2,2,2-trichloroethyl)-formamide, 1-(3,4-dichloroanilino)-1-formylamino-2,2,2-trichloroethane, 2,6-dimethyl-N-tridecyl-morpholine and its salts, 2,6-dimethyl-N-cyclodedecyl-morpholine and its salts, N-[3-(p-tert-butylphenyl)-2-methylpropyl]-cis-2,6-dimethylmorpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidine-methanol, 5-butyl-2-dimethylamino-4-hydroxy-6-methyl-pyrimidine, bis-(p-chlorophenyl)-3-pyridinylmethanol, 1,2-bis-(3-ethoxycarbonyl-2-thioureido)benzene, 1,2-bis-(3-methoxycarbonyl-2-thioureido)benzene, and a variety of fungicides, such as dodecylguanidine acetate, 3-[3-(3,5-dimethyl-2-oxycyclohexyl)-2-hydroxyethyl]-glutarimide, hexachlorobenzene, DL-methyl N-(2,6-dimethylphenyl)-N-furoyl-2-alaninate, DL-methyl N-(2,6-dimethylphenyl)-N-(2'-methoxyacetyl)alaninate, N-(2,6-dimethylphenyl)-N-chloroacetyl-D,L-2-aminobutyrolactone, DL-methyl N-(2,6-dimethylphenyl)-N-(phenylacetyl)alaninate, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine, 1-((bis-(4-fluorophenyl)-methylsilyl)methyl)-1H-1,2,4-triazole.

SYNTHESIS EXAMPLES

The protocols given in the synthesis examples below were used for obtaining further compounds I by using different starting compounds. The compounds thus obtained are listed in the table which follows together with their physical data.

1. Methyl α-(2-(N'-(o-chlorophenyl)-triazolyl-3'-oxymethyl)-phenyl)-β-methoxyacrylate

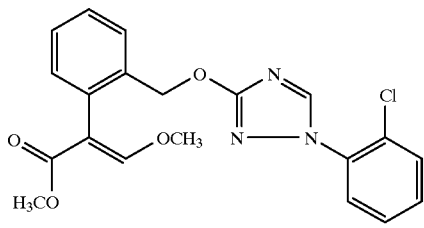

A mixture of 4 g (14 mmol) of methyl α-(o-bromomethylphenyl)-β-methoxyacrylate (EP 203 606), 2.7 g (14 mmol) of N-(o-chlorophenyl)-3-hydroxytriazole and 2.9 g (20 mmol) of $K_2CO_3$ in 10 ml of dimethylformamide was stirred overnight at room temperature (=25° C.). The reaction mixture was subsequently diluted with water and extracted three times using methyl t-butyl ether. The combined organic phases were extracted with water, dried over $MgSO_4$ and concentrated. The residue was purified by column chromatography using cyclohexane/ethyl acetate mixtures. The resulting product crystallized and was extracted by stirring with methyl t-butyl ether. This gave 0.48 g (12%) of the title compound as colorless solid (m.p.=120° C.).

$^1$H NMR (CDCl$_3$; δ in ppm): 8.25 (s, 1H, triazolyl); 7.1–7.8 (9H, phenyl, vinyl); 5.3 (s, 2H, OCH$_2$); 3.8; 3.7 (2s, in each case 3H, 2×OCH$_3$)

2. Methyl α-(3-chloro-2-((1-(2,4-dichlorophenyl)-propyl-3)-oxymethyl)-phenyl)-β-methoxyacrylate

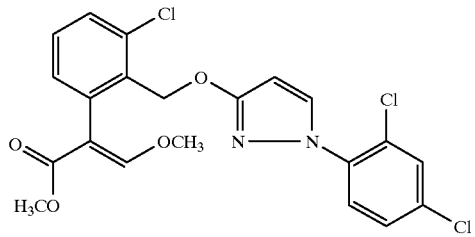

a) Methyl (3-chloro-2-methylphenyl)glyoxylate 30 g of 2,6-dichlorotoluene were reacted with 24 g of Mg filings in 0.6 l of THF to give 3-chloro-2-methylphenylmagnesium chloride. A solution of 152 g of oxalyl chloride in 1 l of THF, cooled to −20 to −25° C., was introduced into the reaction vessel, and the above Grignard solution was added dropwise. After approximately 30 minutes, stirring of the mixture was continued for a further hour at −50° C., and 256 g of methanol were subsequently added dropwise in the course of 2 hours. The mixture was allowed to come to room temperature (=25° C.), the mixture was poured into approximately 3 l of ammonium chloride solution, and this was extracted three times using methyl tert-butyl ether. The combined organic phases were dried over $Na_2SO_4$ and evaporated on a rotary evaporator. This gave 200 g of crude product from which 118 g of the target compound were isolated by means of silica gel chromatography (eluent: toluene).

$^1$H NMR (CDCl$_3$, δ in ppm): 2.6 (s, 3H); 3.9 (s, 3H); 7.25 (dd, 1H); 7.55 (d, 1H); 7.6 (d, 1H)

b) Methyl α-(3-chloro-2-methylphenyl)-β-methoxyacrylate 92.3 g of methoxymethyltriphenylphosphonium chloride were suspended in 500 ml of anhydrous dimethylformamide, and 42.3 g of 30% strength sodium methanolate solution were added. After 20 minutes, a solution of 30 g of methyl 3-chloro-2-methylphenylglyoxylate in 200 ml of dimethylformamide was added dropwise to the pale yellow suspension. After a further 3 hours at room temperature, the mixture was poured into ice-water and extracted three times using methyl tert-butyl ether. It was dried over sodium sulfate, concentrated, and the crude product was applied to 100 g of silica gel. The product was eluted through a silica gel column using methyl tert-butyl ether. This gave 29 g of a colorless solid.

M.p. [°C.]: 66–68; $^1$H NMR (CDCl$_3$, δ in ppm): 2.2 (s, 3H); 3.7 (s, 3H); 3.85 (s, 3H); 7.05 (d, 1H); 7.15 (dd, 1H); 7.35 (d, 1H); 7.55 (s, 1H)

c) Methyl α-(2-bromomethyl-3-chlorophenyl)-β-methoxyacrylate 27.0 g of methyl α-(3-chloro-2-methylphenyl)-β-methoxyacrylate and 21.5 g of N-bromosuccinimide were stirred in 300 ml of anhydrous tetrachloromethane. After 1 g of Porofor N had been added, the mixture was refluxed for 4 hours. After cooling to room temperature (=25° C.), the succinimide was removed. The combined organic phases were washed with water, dried over sodium sulfate and concentrated. This gave 23 g of the title compound as colorless crystals.

M.p. [°C.]: 66–68; $^1$H NMR (CDCl$_3$, δ in ppm): 3.75 (s, 3H); 3.85 (s, 3H); 4.5 (broad, 2H); 7.05 (d, 1H); 7.2 (dd, 1H); 7.4 (d, 1H); 7.65 (s, 1H)

d) Methyl α-(3-chloro-2-[(1-[2,4-dichlorophenyl]-pyrazol-3-yl)-oxymethyl]phenyl-β-methoxyacrylate 1.6 g of 1-(2,4-dichlorophenyl)-3-hydroxypyrazole and 0.97 g of potassium carbonate in 20 ml of dimethylformamide were stirred for approximately 30 minutes. A solution of 2.23 g of methyl α-(2-bromomethyl-3-chlorophenyl)-β-methoxyacrylate in 20 ml of dimethylformamide was then added. After a few hours at room temperature, the batch was heated at 60° C. for 4 hours. For working-up, it was poured into ice-water and extracted three times using methyl tert-butyl ether. The combined organic phases were dried over sodium sulfate and concentrated, the crude product was chromatographed over silica gel (eluent toluene). This gave 1.7 g of the title compound as a viscous oil.

$^1$H NMR (CDCl$_3$, δ in ppm): 3.7 (s, 3H); 3.8 (s, 3H); 5.35 (s, 2H); 5.9 (d, 1H); 7.1–7.5 (m, 5H); 7.55 (s, 1H); 7.6 (d, 1H); 7.7 (d, 1H)

TABLE

| No. | R$_n$ | R$^1$ | R$^2$ | * | R$^b_m$/R$^c_o$/R$^d$ | R$^a$ | Physical data$^a$ |
|---|---|---|---|---|---|---|---|
| 01 | — | CH$_3$ | CH$_3$ | A.1 | — | 4-Cl—C$_6$H$_4$ | 104 |
| 02 | — | CH$_3$ | CH$_3$ | A.1 | — | 4-CH$_3$—C$_6$H$_4$ | 94 |
| 03 | 3-Cl | CH$_3$ | CH$_3$ | A.1 | — | 4-Cl—C$_6$H$_4$ | 2950, 1707, 1634, 1545, 1482, 1126 |
| 04 | 3-Cl | CH$_3$ | CH$_3$ | A.1 | — | 2,4-Cl$_2$—C$_6$H$_3$ | 2940, 1709, 1548, 1261, 1127 |
| 05 | — | CH$_3$ | CH$_3$ | A.1 | — | 3-CF$_3$-pyridin-6-yl | 79 |
| 06 | — | CH$_3$ | CH$_3$ | A.1 | — | 4-OCF$_3$—C$_6$H$_4$ | 2940, 1707, 1548, 1258, 1130 |
| 07 | — | CH$_3$ | CH$_3$ | A.1 | — | pyrazin-2-yl | 122 |
| 08 | — | CH$_3$ | CH$_3$ | A.1 | — | CH$_2$-[4-Cl—C$_6$H$_4$] | 2940, 1728, 1537, 1492, 1070, 1016 |
| 09 | — | CH$_3$ | CH$_3$ | A.1 | — | 2-Cl-pyridin-6-yl | 2950, 1707, 1588, 1550, 1450, 1129 |
| 10 | — | CH$_3$ | CH$_3$ | A.1 | — | CH$_2$-[2,4-Cl$_2$—C$_6$H$_3$] | 2955, 1709, 1539, 1256, 1130 |
| 11 | — | CH$_3$ | CH$_3$ | A.3 | — | C$_6$H$_5$ | 7.6(1H); 3.8(3H); 3.7(3H) |
| 12 | — | CH$_3$ | CH$_3$ | A.3 | — | 2-Cl—C$_6$H$_4$ | 129 |
| 13 | — | CH$_3$ | CH$_3$ | A.3 | — | 3-Cl—C$_6$H$_4$ | 90 |
| 14 | — | CH$_3$ | CH$_3$ | A.3 | — | 3-CF$_3$-pyridin-6-yl | 102 |
| 15 | — | CH$_3$ | CH$_3$ | A.3 | CH$_3$ | 3-CF$_3$-pyridin-6-yl | 88 |
| 16 | — | CH$_3$ | CH$_3$ | A.3 | — | 2,4-Cl$_2$—C$_6$H$_3$ | 103 |
| 17 | — | CH$_3$ | CH$_3$ | A.2 | — | 4-Cl—C$_6$H$_4$ | 2940, 1694, 1636, 1500, 1251, 1132 |
| 18 | — | CH$_3$ | CH$_3$ | A.1 | — | 2-Cl, 4-F—C$_6$H$_3$ | 93 |
| 19 | — | CH$_3$ | CH$_3$ | A.1 | — | 2,4-Cl$_2$—C$_6$H$_3$ | 99 |
| 20 | — | CH$_3$ | CH$_3$ | A.1 | — | 3-Cl-pyridin-6-yl | 95 |
| 21 | — | CH$_3$ | CH$_3$ | A.1 | — | 2,4-F$_2$—C$_6$H$_3$ | 109 |
| 22 | — | CH$_3$ | CH$_3$ | A.2 | — | C$_6$H$_5$ | 2945, 1702, 1633, 1502, 1253, 1128 |
| 23 | — | CH$_3$ | CH$_3$ | A.2 | 3-CH$_3$ | C$_6$H$_5$ | 1706, 1634, 1504, 1189, 1129 |
| 24 | — | CH$_3$ | CH$_3$ | A.2 | 3-CH$_3$ | 4-Cl—C$_6$H$_4$ | 102–104 |
| 25 | — | CH$_3$ | CH$_3$ | A.2 | 5-CH$_3$ | 4-Cl—C$_6$H$_4$ | 64–97 |
| 26 | — | CH$_3$ | CH$_3$ | A.3 | — | 4-Cl—C$_6$H$_4$ | 1707, 1544, 1501, 1257, 1130 |
| 27 | — | CH$_3$ | CH$_3$ | A.1 | — | 3-Cl-pyridin-2-yl | 1707, 1633, 1549, 1455, 1130 |
| 28 | — | CH$_3$ | CH$_3$ | A.1 | — | 3-Br—C$_6$H$_4$ | 75–77 |
| 29 | — | CH$_3$ | CH$_3$ | A.1. | — | 4-Br—C$_6$H$_4$ | 101–102 |
| 30 | — | CH$_3$ | CH$_3$ | A.1 | — | 4-I—C$_6$H$_4$ | 1708, 1546, 1478, 1256, 1130 |
| 31 | — | CH$_3$ | CH$_3$ | A.1 | — | 2-Cl, 4-I—C$_6$H$_3$ | 110–112 |
| 32 | — | CH$_3$ | CH$_3$ | A.1 | — | 3-CN—C$_6$H$_4$ | 119–120 |
| 33 | — | CH$_3$ | CH$_3$ | A.1 | — | 4-CN—C$_6$H$_4$ | 112–113 |
| 34 | — | CH$_3$ | CH$_3$ | A.1 | — | 4-(NCH$_3$-3-CH$_3$-pyrazol-5-yl)-C$_6$H$_4$ | 99–102 |
| 35 | — | CH$_3$ | CH$_3$ | A.1 | — | 3-Cl, 4-(NCH$_3$-3-CH$_3$-pyrazol-5-yl)-C$_6$H$_3$ | 133–135 |
| 36 | — | CH$_3$ | CH$_3$ | A.1 | — | 2-CH$_3$, 4-F—C$_6$H$_3$ | 84–85 |
| 37 | — | CH$_3$ | CH$_3$ | A.1 | — | 2-Br—C$_6$H$_4$ | 1706, 1633, 1544, 1256, 1129 |
| 38 | — | CH$_3$ | CH$_3$ | A.1 | — | 3-Cl, 4-Br—C$_6$H$_3$ | 1706, 1548, 1472, 1256, 1129 |
| 39 | — | CH$_3$ | CH$_3$ | A.1 | — | 3-Cl, 4-CN—C$_6$H$_3$ | 2213, 1706, 1602, 1549, 1130 |
| 40 | — | CH$_3$ | CH$_3$ | A.1 | — | 3-Cl, 5-CF$_3$-pyridin-2-yl | 71–73 |
| 41 | — | CH$_3$ | CH$_3$ | A.3 | — | 2-CH$_3$, 4-Cl—C$_6$H$_3$ | 1705, 1541, 1479, 1256, 1130 |
| 42 | — | CH$_3$ | CH$_3$ | A.3 | — | 4-CH(CH$_3$)$_2$—C$_6$H$_4$ | 1707, 1542, 1257, 1130 |
| 43 | — | CH$_3$ | CH$_3$ | A.3 | — | 2,4-(CH$_3$)$_2$—C$_6$H$_3$ | 1706, 1540, 1256, 1130, 1109 |
| 44 | — | CH$_3$ | CH$_3$ | A.3 | — | 4-CF$_3$—C$_6$H$_4$ | 1707, 1547, 1319, 1256, 1128 |
| 45 | — | CH$_3$ | CH$_3$ | A.3 | — | 4-C(CH$_3$)$_3$—C$_6$H$_4$ | 1634, 1543, 1257, 1130 |
| 46 | — | CH$_3$ | CH$_3$ | A.1 | — | 4-COCH$_3$—C$_6$H$_4$ | 114–116 |
| 47 | — | CH$_3$ | CH$_3$ | A.1 | — | 2-Cl, 4-COCH$_3$—C$_6$H$_3$ | 114–117 |
| 48 | — | CH$_3$ | CH$_3$ | A.1 | — | 4-[C(CH$_3$)=NOCH$_3$]—C$_6$H$_4$ | 1707, 1547, 1256, 1130, 1050 |

TABLE-continued

| No. | $R_n$ | $R^1$ | $R^2$ | * | $R^b_m/R^c_o/R^d$ | $R^a$ (R³) | Physical data[a] |
|---|---|---|---|---|---|---|---|
| 49 | — | $CH_3$ | $CH_3$ | A.1 | — | 4-[C(CH$_3$)=NOCH$_2$CH$_3$]—C$_6$H$_4$ | 1.3(3H); 2.2(3H); 3.65 (3H); 3.8(3H); 4.25(2H); 5.2(2H); 5.9(1H); 7.1–7.8(10H) |
| 50 | — | $CH_3$ | $CH_3$ | A.1 | — | 2-Cl, 4-[C(CH$_3$)=NOCH$_3$]—C$_6$H$_3$ | 1708, 1634, 1545, 1256, 1051 |
| 51 | — | $CH_3$ | $CH_3$ | A.1 | — | 2-Cl, 4-[C(CH$_3$)=NOCH$_2$CH$_3$]—C$_6$H$_3$ | 1708, 1634, 1545, 1129, 1050 |
| 52 | — | $CH_3$ | $CH_3$ | A.1 | — | 2-Br, 4-Cl—C$_6$H$_3$ | 1707, 1634, 1546, 1475, 1130 |
| 53 | — | $CH_3$ | $CH_3$ | A.1 | — | 3-Cl, 4-CH$_3$—C$_6$H$_3$ | 1706, 1633, 1545, 1255, 1129 |
| 54 | — | $CH_3$ | $CH_3$ | A.1 | — | 3,4-(CH$_3$)$_2$—C$_6$H$_3$ | 1707, 1638, 1543, 1355, 1130 |
| 55 | — | $CH_3$ | $CH_3$ | A.1 | — | 4-CH$_3$CH$_3$—C$_6$H$_4$ | 1707, 1634, 1544, 1256, 1130 |
| 56 | — | $CH_3$ | $CH_3$ | A.1 | — | 4-CH(CH$_3$)$_2$—C$_6$H$_4$ | 1708, 1634, 1545, 1256, 1130 |
| 57 | — | $CH_3$ | $CH_3$ | A.1 | — | 4-OC$_6$H$_5$—C$_6$H$_4$ | 1707, 1545, 1488, 1484, 1297 |
| 58 | — | $CH_3$ | $CH_3$ | A.1 | 5-CF$_3$ | CH(CH$_3$)$_2$ | 68–70 |
| 59 | 4-OCH$_3$ | $CH_3$ | $CH_3$ | A.1 | — | 4-Cl—C$_6$H$_4$ | 75–78 |

[a]M.p. (° C.); ¹H-NMR (ppm); IR (cm⁻¹)
*Substructure of $R^3$

Examples for the action against fungal pests

The fungicidal action of the compounds of the formula I was demonstrated by the following experiments:

The active ingredients were prepared as a 20% emulsion in a mixture of 70% by weight of cyclohexanone, 20% by weight of Nekanil® LN (Lutensol® AP6, wetting agent with emulsifying and dispersing action based on ethoxylated alkylphenols) and 10% by weight of Emulphor® EL (Emulan® EL, emulsifier based on ethoxylated fatty alcohols) and diluted with water to give the desired concentration.

Action against *Plasmopara viticola* (downy mildew of grape vine)

Potted grape vines (variety: "Müller Thurgau") were sprayed to run off point with the preparation of active ingredient (application rate: 16 ppm). After 8 days, the plants were sprayed with a zoo spore suspension of the fungus *Plasmopara viticola* and kept for 5 days at 20–30° C. and high atmospheric humidity. Prior to assessment, the plants were then kept at high atmospheric humidity for 16 hours. They were assessed visually.

In this test, the disease level of the plants which had been treated with compound Nos. 1–6, 8, 10–13 and 16–22 according to the invention was 15% or less, while the disease level of the untreated (control) plants was 70%.

In a corresponding test, the disease level of the plants which had been treated with compounds 23, 24, 26–34, 36–38 and 40–58 according to the invention was 15% or less, while the disease level of the untreated (control) plants was 70%.

Action against *Puccinia recondita* (leaf rust of wheat)

Leaves of wheat seedlings (variety "Kanzler") were dusted with leaf rust spores (*Puccinia recondita*). The treated plants were incubated for 24 hours at 20–22° C. and a relative atmospheric humidity of 90–95% and subsequently treated with the aqueous preparation of active ingredient (application rate: 63 ppm). After a further 8 days at 20–22° C. and a relative atmospheric humidity of 65–70%, the extent of fungal development was determined. The plants were assessed visually.

In this test, the disease level of the plants which had been treated with compound Nos. 1–6, 9–11 and 13–21 according to the invention was 15% or less, while the disease level of the untreated (control) plants was 65%.

In a corresponding test, the disease level of the plants which had been treated with compounds 24–32, 36–38, 40–45, 48–50, 52–57 and 59 according to the invention was 15% or less, while the disease level of the untreated (control) plants was 65%.

Action against *Pyricularia oryzae* (rice blast)

Rice seedlings (variety: "Tai Nong 67") were sprayed to run off point with the preparation of active ingredient (application rate: 63 ppm). After 24 hours, the plants were sprayed with an aqueous spore suspension of the fungus *Pyricularia oryzae* and kept for 6 days at 22–24° C. at a relative atmospheric humidity of 95–99%. The plants were assessed visually.

In this test, the disease level of the plants which had been treated with compound Nos. 1–6, 9–11, 13–16, 19 and 21 according to the invention was 15% or less, while the disease level of the untreated (control) plants was 85%.

In a corresponding test, the disease level of the plants which had been treated with compounds 24, 26, 27, 30–33, 37–42, 49, 50 and 52–58 according to the invention was 15% or less, while the disease level of the untreated (control) plants was 65%.

Examples for the action against animal pests

The action of the compounds of the general formula I against animal pests was demonstrated by the following experiments:

The active ingredients were prepared a) as a 0.1% strength solution in acetone or b) as a 10% strength emulsion in a mixture of 70% by weight of cyclohexanone, 20% by weight of Nekanil® LN (Lutensol® AP6, wetting agent with emulsifying and dispersing agent based on ethoxylated alkylphenols) and 10% by weight of Emulphor® EL (Emulan® EL, emulsifier based on ethoxylated fatty alcohols) and diluted to the desired concentration, in the case of a) with acetone and in the case of b) with water.

After the experiments had been concluded, the lowest concentration at which each of the compounds was still capable of causing an 80–100% inhibition or mortality in comparison to untreated controls was determined (critical or minimal concentration).

*Aphis fabae* (black bean aphid), contact action

Severely infested dwarf beans (Vicia faba) were treated with the aqueous preparation of active ingredient. The mortality was assessed after 24 hours.

In this test, compounds 29, 54 and 56–58 had limit concentrations of 400 ppm and less.

*Nephotettix cincticeps* (green rice leafhopper), contact action

Filter disks were treated with the aqueous preparation of active ingredient and subsequently populated with 5 adult leafhoppers. The mortality was assessed after 24 h ours.

In this test, compounds 25, 27, 38, 44 and 59 had limit concentrations of 0.4 mg and less.

*Prodenia litura* (Egyptian cotton leafworm), contact action

Filters which had been treated with the aqueous preparation of active ingredient were populated with 5 caterpillars. The first assessment was carried out after 4 hours. If at least one caterpillar is still alive, a feed mix is added. The mortality is determined after 24 hours.

In this test, compounds 24, 30 and 38 had limit concentrations of 0.4 mg and less.

*Tetranychus telarius* (greenhouse red spider mite), contact action

Severely infested dwarf beans in pots which had developed the second pair of true leaves were treated with the aqueous preparation of active ingredient. After 5 days in the greenhouse, the degree of control was determined by means of a stereo microscope.

In this test, compounds 25, 30, 31, 41 and 52–59 had limit concentrations of 400 ppm and less.

We claim:

1. A compound of the formula I

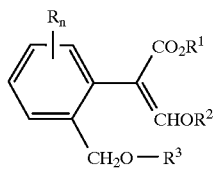

in which n and the substituents have the following meanings:

n is 0, 1, 2, 3, or 4, where the substituents R may be different if n is 2, 3, or 4;

R is nitro, cyano, halogen,
  unsubstituted or substituted alkyl, alkenyl, alkynyl, alkoxy, alkenyloxy, alkynyloxy or
  in the event that n is greater than 1 additionally an unsubstituted or substituted bridge which is bonded to two adjacent ring atoms and which comprises three to four members selected from the group consisting of 3 or 4 carbon atoms, 1, 2 or three carbon atoms and 1 or 2 nitrogen, oxygen and sulfur atoms, it being possible for this bridge, together with the ring to which it is bonded, to form a partially unsaturated or aromatic radical;

$R^1$, $R^2$ are $C_1$–$C_4$-alkyl;

$R^3$ is a pyrazole radical of the formula A.1

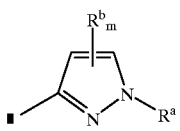

the bond marked with ■ being the bond to the oxygen, and m and the substituents having the following meanings:

$R^a$ is a substituted mono- or binuclear aromatic radical which, besides carbon atoms, may contain one to four nitrogen atoms or one or two nitrogen atoms and one or two oxygen or sulfur atoms or one oxygen or one sulfur atom as ring members;

m is 0, 1 or 2, where the substituents $R^b$ may be different if m is 2;

$R^b$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl.

2. The compound of claim 1, wherein $R^a$ is substituted aryl.

3. A process for the preparation of the compound of claim 1, which comprises reacting a benzyl compound of the formula II

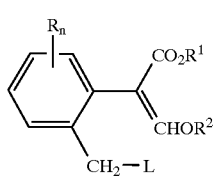

where L is a nucleophilically exchangeable group, with a hydroxyazole of the formula III $$HO—R^3 \qquad III$$

in the presence of a base.

4. A mixture suitable for controlling fungal pests, comprising an inert additive and an effective amount of the compound of claim 1.

5. A mixture suitable for controlling animal pests, comprising an inert additive and an effective amount of the compound of claim 1.

6. A compound of the formula IV

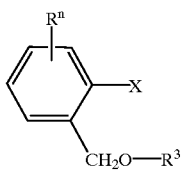

where

X is $CH_2CN$, $CH_2CO_2R^1$ and $C(=O)CO_2CH_3$, n is 0, 1, 2, 3, or 4, where the substituents R may be different if n is 2, 3, or 4;

R is nitro, cyano, halogen,
  unsubstituted or substituted alkyl, alkenyl, alkynyl, alkoxy, alkenyloxy, alkynyloxy or
  in the event that n is greater than 1 additionally an unsubstituted or substituted bridge which is bonded to two adjacent ring atoms and which comprises three to four members selected from the group consisting of 3 or 4 carbon atoms, 1, 2 or three carbon atoms and 1 or 2 nitrogen, oxygen and sulfur atoms, it being possible for this bridge, together with the ring to which it is bonded, to form a partially unsaturated or aromatic radical;

$R^1$ is $C_1$–$C_4$-alkyl;

$R^3$ is a pyrazole radical of the formula A.1

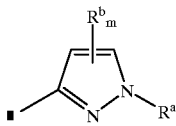

A.1 the bond marked with ■ being the bond to the oxygen, and m and the substituents having the following meanings:

$R^a$ is a substituted mono- or binuclear aromatic radical which, besides carbon atoms, may contain one to four nitrogen atoms or one or two nitrogen atoms and one or two oxygen or sulfur atoms or one oxygen or one sulfur atom as ring members;

m is 0, 1 or 2, where the substituents $R^b$ may be different if m is 2;

$R^b$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl.

7. A method of controlling fungal pests, which comprises treating the fungal pests, their environment or the plants, areas, materials or rooms to be protected against fungal pests with an effective amount of the compound of claim 1.

8. A method of controlling animal pests, which comprises treating the pests, their environment or the plants, areas, materials or rooms to be protected against the pests with an effective amount of the compound of claim 1.

9. The compound of claim 1, wherein $R^a$ is substituted phenyl.

* * * * *

UNITED STATES PATENT AND TRADEMARK OFFICE
CERTIFICATE OF CORRECTION

PATENT NO.: 5,935,986

DATED: August 10, 1999

INVENTOR(S): MUELLER et al.

It is certified that error appears in the above-identified patent and that said Letters Patent is hereby corrected as shown below:

In the abstract, after formula A.2 insert formula A.3 as follows:

-- 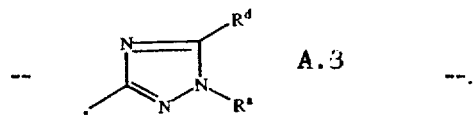 --.

Signed and Sealed this

Twenty-fifth Day of January, 2000

Attest:

Attesting Officer

*Acting Commissioner of Patents and Trademarks*